(12) United States Patent
Shiba et al.

(10) Patent No.: US 9,017,669 B2
(45) Date of Patent: *Apr. 28, 2015

(54) ANTI-CDH3 ANTIBODIES AND USES THEREOF

(75) Inventors: Yasuhiro Shiba, Kanagawa (JP); Hiroki Yoshioka, Kanagawa (JP); Shinji Yamamoto, Kanagawa (JP); Aiko Kudo, Kanagawa (JP); Ryuji Ohsawa, Kanagawa (JP); Pohsing Ng, Kanagawa (JP); Yusuke Nakamura, Tokyo (JP); Keigo Endo, Gunma (JP)

(73) Assignee: OncoTherapy Science, Inc., Kanagawa (JP)

(*) Notice: Subject to any disclaimer, the term of this patent is extended or adjusted under 35 U.S.C. 154(b) by 198 days.

This patent is subject to a terminal disclaimer.

(21) Appl. No.: 13/519,127

(22) PCT Filed: Dec. 28, 2009

(86) PCT No.: PCT/JP2009/007333
§ 371 (c)(1),
(2), (4) Date: Oct. 9, 2012

(87) PCT Pub. No.: WO2011/080796
PCT Pub. Date: Jul. 7, 2011

(65) Prior Publication Data
US 2013/0034566 A1   Feb. 7, 2013

(51) Int. Cl.
| | | |
|---|---|---|
| *C07K 16/00* | (2006.01) | |
| *C07K 16/46* | (2006.01) | |
| *C07K 16/28* | (2006.01) | |
| *A61K 39/395* | (2006.01) | |
| *G01N 33/53* | (2006.01) | |
| *A61K 51/10* | (2006.01) | |
| *C07K 16/06* | (2006.01) | |
| *G01N 33/574* | (2006.01) | |
| *A61K 39/00* | (2006.01) | |

(52) U.S. Cl.
CPC .............. *C07K 16/28* (2013.01); *A61K 51/1027* (2013.01); *A61K 2039/505* (2013.01); *C07K 16/065* (2013.01); *C07K 2317/41* (2013.01); *C07K 2317/56* (2013.01); *G01N 33/574* (2013.01); *G01N 2333/705* (2013.01)

(58) Field of Classification Search
None
See application file for complete search history.

(56) References Cited

U.S. PATENT DOCUMENTS

| | | | | |
|---|---|---|---|---|
| 7,709,610 | B2 * | 5/2010 | Williams et al. | 530/388.15 |
| 8,435,749 | B2 * | 5/2013 | Togashi et al. | 435/7.1 |
| 2002/0141990 | A1 * | 10/2002 | Deen et al. | 424/133.1 |
| 2005/0214836 | A1 | 9/2005 | Nakamura et al. | |
| 2005/0260639 | A1 | 11/2005 | Nakamura et al. | |
| 2006/0024692 | A1 | 2/2006 | Nakamura et al. | |
| 2006/0105333 | A1 | 5/2006 | Nakamura et al. | |
| 2006/0194199 | A1 | 8/2006 | Nakamura et al. | |
| 2006/0199179 | A1 | 9/2006 | Nakamura et al. | |
| 2009/0162361 | A1 | 6/2009 | Nakamura et al. | |
| 2009/0169572 | A1 | 7/2009 | Nakatsuru et al. | |
| 2009/0175844 | A1 | 7/2009 | Nakamura et al. | |
| 2009/0317400 | A1 * | 12/2009 | Masternak et al. | 424/142.1 |
| 2010/0040641 | A1 | 2/2010 | Tsunoda et al. | |
| 2011/0165184 | A1 | 7/2011 | Nishimura et al. | |
| 2011/0280898 | A1 | 11/2011 | Tsunoda et al. | |
| 2012/0014996 | A1 | 1/2012 | Nakamura et al. | |
| 2012/0128584 | A1 | 5/2012 | Togashi et al. | |

FOREIGN PATENT DOCUMENTS

| | | |
|---|---|---|
| CN | 101432303 A | 5/2009 |
| JP | 2007-224009 A | 9/2007 |
| JP | 2007-530431 A | 11/2007 |
| JP | 2009-528257 A | 8/2009 |
| WO | 94/12625 A2 | 6/1994 |
| WO | 02/097395 A2 | 12/2002 |
| WO | 04/001072 A2 | 12/2003 |
| WO | 2004/007770 A2 | 1/2004 |
| WO | 2004/024952 A1 | 3/2004 |
| WO | 2004/031410 A2 | 4/2004 |
| WO | 2004/031412 A2 | 4/2004 |
| WO | 2004/031413 A2 | 4/2004 |
| WO | 2004/110345 A2 | 12/2004 |
| WO | 2005/090572 A2 | 9/2005 |
| WO | 2006/085684 A2 | 8/2006 |
| WO | 2006/114704 A2 | 11/2006 |
| WO | 2007/102525 A1 | 9/2007 |
| WO | 2008/102557 A1 | 8/2008 |
| WO | 2009/025116 A1 | 2/2009 |
| WO | 2010/001585 A1 | 1/2010 |
| WO | 2010/021111 A1 | 2/2010 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91.*

Vajdos et al. Comprehensive functional maps of the antigen-binding site of an anti-ErbB2 antibody obtained with shotgun scanning mutagenesis. J. Mol. Biol., Jul. 5, 2002, 320(2):415-28.*

Baselga, "Herceptin® Alone or in Combination with Chemotherapy in the Treatment of HER2-Positive Metastatic Breast Cancer: Pivotal Trials," *Oncology*, 61 Suppl 2, pp. 14-21 (2001).

Behrens, "Cadherins and catenins: Role in signal transduction and tumor progression," *Cancer Metastasis Rev.*, vol. 18(1), pp. 15-30 (1999).

Conacci-Sorrell, et al., "The cadherin-catenin adhesion system in signaling and cancer," *J Clin Invest.*, vol. 109(8), pp. 987-991 (Apr. 2002).

(Continued)

*Primary Examiner* — Maher Haddad

(57) ABSTRACT

The present invention relates to anti-CDH3 antibodies, which can be labeled with a radioisotope. Moreover, the present invention provides methods and pharmaceutical compositions that comprise an anti-CDH3 antibody as an active ingredient. Since CDH3 is strongly expressed in pancreatic, lung, colon, prostate, breast, gastric or liver cancer cells, the present invention is useful in pancreatic, lung, colon, prostate, breast, gastric or liver cancer therapies.

19 Claims, 2 Drawing Sheets

(56) References Cited

OTHER PUBLICATIONS

Crist, et al. "Intergroup Rhabdomyosarcoma Study—IV: Results for Patient With Nonmetastatic Disease," *J Clin Oncol.*, vol. 19(12), pp. 3091-3102 (Jun. 15, 2001).

Daniel, et al., "Expression and Functional Role of E- and P-Cadherins in Mouse Mammary Ductal Morphogenesis and Growth," *Dev Viol.*, vol. 169(2), pp. 511-519 (Jun. 1995).

Ferguson, et al., "Current Treatment of Osteosarcoma," *Cancer Invest.*, vol. 19(3), pp. 292-315 (2001).

Ferrara, et al., "Discovery and Development of Bevacizumab, an Anti-Vegf Antibody for Treating Cancer," *Nat Rev Drug Discov.*, vol. 3(5), pp. 391-400 (May 2004).

Gamallo, et al., "The Prognostic Significance of P-Cadherin in Infiltrating Ductal Breast Carcinoma," *Mod Pathol.*, vol. 14(7), pp. 650-654 (Jul. 2001).

Harris, "Monoclonal antibodies as therapeutic agents for cancer," *Lancet Oncol.*, vol. 5(5), pp. 292-302 (May 2004).

Kinuya, Nippon Hoshasen Gijutsu Gakkai Zasshi, vol. 65(5), pp. 659-667 (May 20, 2009).

Maloney et al., "IDEC-C2B8 (Rituximab) Anti-CD20 Monoclonal Antibody Therapy in Patients With Relapsed Low-Grade Non-Hodgkin's Lymphoma," *Blood*, vol. 90(6), pp. 2188-2195 (Sep. 15, 1997).

Mattes, et al., Therapy of Advanced B-Lymphoma Xenografts with a Combination of $^{90}$Y-anti-CD22 IgG (Epratuzumab) and Unlabeled Anti-CD20 IgG (Veltuzumab), *Clin Cancer Res.*, vol. 14(19), pp. 6154-6160 (Oct. 1, 2008).

Nose, et al., "A Novel Cadherin Cell Adhesion Molecule: Its Expression Patterns Associated with Implantation and Organogenesis of Mouse Embryos," *J Cell Biol.*, vol. 103(6 Pt 2), pp. 2649-2658 (Dec. 1986).

Nose, et al., "Expressed Recombinant Cadherins Mediate Cell Sorting in Model Systems," *Cell*, vol. 54(7), pp. 993-1001 (Sep. 23, 1988).

Pagel, et al., "Pretargeted Radioimmunotherapy Using Anti-CD45 Monoclonal Antibodies to Deliver Radiation to Murine Hematolymphoid Tissues and Human Myeloid Leukemia," *Cancer Res.*, vol. 69(1), pp. 185-192 (Jan. 1, 2009).

Shimoyama, et al., Cancer Res., "Cadherin Cell-Adhesion Molecules in Human Epitehlial Tissues and Carcinomas," *Cancer Res.*, vol. 49(8), pp. 2128-2133 (Apr. 15, 1989).

Stefansson, et al., "Prognostic Impact of Alterations in P-Cadherin Expression and Related Cell Adhesion Markers in Endometrial Cancer," *J Clin Oncol.*, vol. 22(7), pp. 1242-1252 (Apr. 1, 2004).

Steinberg, et al., "Experimental specification of cell sorting, tissue spreading, and specific spatial patterning by quantitative differences in cadherin expression," *Proc Natl Acad Sci USA*, vol. 91(1), pp. 206-209 (Jan. 4, 1994).

Takeichi, "The cadherins: cell-cell adhesion molecules controlling animal morphogenesis," *Development*, vol. 102(4), pp. 639-655 (Apr. 1988).

Takeichi, "Cadherin Cell Adhesion Receptor as a Morphogenetic Regulator," *Science*, vol. 251(5000), pp. 1451-1455 (Mar. 22, 1991).

Wunder, et al., "The Histological Response to Chemotherapy as a Predictor of the Oncological Outcome of Operative Treatment of Ewing Sarcoma," *J Bone Joint Surg Am.*, vol. 80(7), pp. 1020-1033 (Jul. 1998).

U.S. Appl. No. 13/464,831, filed May 4, 2012, 162 pages.
U.S. Appl. No. 13/536,327, filed Jun. 28, 2012, 204 pages.
International Search Report and Written Opinion for PCT/JP2009/007333, mailed Feb. 9, 2010, 13 pages.
U.S. Appl. No. 13/744,354, filed Jan. 17, 2013, 124 pages.
U.S. Appl. No. 14/079,144, filed on Nov. 13, 2013, 159 pages.
U.S. Appl. No. 14/274,373, filed on May 9, 2014, 123 pages.

\* cited by examiner

SEQUENCE LISTING

<160> NUMBER OF SEQ ID NOS: 88

<210> SEQ ID NO 1
<211> LENGTH: 4276
<212> TYPE: DNA
<213> ORGANISM: Homo sapiens

<400> SEQUENCE: 1
tgcgttttaa aaattgtctt tatttacatt ttacagaaag ttgagaaagt gttatttata        60

| | |
|---|---|
| tgggggggtag gggtgctgga gattatgaga ctaataacaa ccctcttagc tcgcacccctt | 120 |
| tggcaccact acagcttcca aactctggga ctttctcgac tagcttccct ttgtttagct | 180 |
| gtgaaatgga agaagcggtc cgggtgtggc ggctcatgcc tgtaacctga gcactctggg | 240 |
| aggcggagga tcgcttgagt ccagaagttc aagaccagct gggcaacat agggtgaccc | 300 |
| tccaccctcc ccccgcccca ccacatcgct acaaaaaatt tttaaaaatt agccgggtgt | 360 |
| ggtggcgcaa gcctgtagtc tcagcggag ctgaggagg agaatcgctt cagcccggga | 420 |
| ggtcgaggct gtagtgagcc gagatcgcgc tactgcactc ctgggcgaca gagcgagacc | 480 |
| ctgtctccaa aaaaaaaaa aaagaaaaa agaggaagtt gtatccaatt cagaaacgcg | 540 |
| gtccttcggg acctgctagt tttataccccc ggaggatcct ccccggcggg ctggcacggg | 600 |
| aggtggagaa agaggcttgg gcggcccccgc tgtagccgcg tgtgggagga cgcacgggcc | 660 |
| tgcttcaaag ctttgggata acagcgcctc cgggggataa tgaatgcgga gcctccgttt | 720 |
| tcagtcgact tcagatgtgt ctccactttt ttccgctgta gccgcaaggc aaggaaacat | 780 |
| ttctcttccc gtactgagga ggctgaggag tgcactgggt gttcttttct cctctaaccc | 840 |
| agaactgcga gacagaggct gagtccctgt aaagaacagc tccagaaaag ccaggagagc | 900 |
| gcaggagggc atccgggagg ccaggagggg ttcgctgggg cctcaaccgc acccacatcg | 960 |
| gtcccacctg cgagggggcg ggacctcgtg gcgctggacc aatcagcacc cacctgcgct | 1020 |
| cacctggcct cctcccgctg gctcccgggg gctgcggtgc tcaaagggggc aagagctgag | 1080 |
| cggaacaccg gcccgccgtc gcggcagctg cttcacccct ctctctgcag ccatggggct | 1140 |
| ccctcgtgga cctctcgcgt ctctcctcct tctccaggtt tgctggctgc agtgcgcggc | 1200 |
| ctccgagccg tgccgggcgg tcttcaggga ggctgaagtg accttggagg cgggaggcgc | 1260 |
| ggagcaggag cccggccagg cgctggggaa agtattcatg ggctgccctg gcaagagcc | 1320 |
| agctctgttt agcactgata atgatgactt cactgtgcgg aatggcgaga cagtccagga | 1380 |
| aagaaggtca ctgaaggaaa ggaatccatt gaagatcttc ccatccaaac gtatcttacg | 1440 |
| aagacacaag agagattggg tggttgctcc aatatctgtc cctgaaaatg gcaagggtcc | 1500 |
| cttcccccag agactgaatc agctcaagtc taataaagat agagacacca agatttttcta | 1560 |
| cagcatcacg gggccggggg cagacagccc ccctgagggt gtcttcgctg tagagaagga | 1620 |
| gacaggctgg ttgttgttga ataagccact ggaccgggag gagattgcca agtatgagct | 1680 |
| cttttggccac gctgtgtcag agaatggtgc ctcagtggag gaccccatga acatctccat | 1740 |
| catcgtgacc gaccagaatg accacaagcc caagtttacc caggacaccct tccgagggag | 1800 |
| tgtcttagag ggagtcctac caggtacttc tgtgatgcag gtgacagcca cggatgagga | 1860 |
| tgatgccatc tacacctaca atgggggtggt tgcttactcc atccatagcc aagaaccaaa | 1920 |
| ggacccacac gacctcatgt tcaccattca ccggagcaca ggcaccatca gcgtcatctc | 1980 |
| cagtggcctg gaccgggaaa aagtccctga gtacacactg accatccagg ccacagacat | 2040 |
| ggatgggggac ggctccacca ccacggcagt ggcagtagtg gagatccttg atgccaatga | 2100 |
| caatgctccc atgtttgacc cccagaagta cgaggcccat gtgcctgaga atgcagtggg | 2160 |
| ccatgaggtg cagaggctga cggtcactga tctggacgcc cccaactcac cagcgtggcg | 2220 |
| tgccacctac cttatcatgg gcggtgacga cggggaccat tttaccatca ccacccaccc | 2280 |
| tgagagcaac cagggcatcc tgacaaccag gaagggtttg gatttttgagg ccaaaaacca | 2340 |
| gcacacccctg tacgttgaag tgaccaacga ggcccctttt gtgctgaagc tcccaacctc | 2400 |

```
cacagccacc atagtggtcc acgtggagga tgtgaatgag gcacctgtgt tgtcccacc    2460
ctccaaagtc gttgaggtcc aggagggcat ccccactggg gagcctgtgt gtgtctacac  2520
tgcagaagac cctgacaagg agaatcaaaa gatcagctac cgcatcctga gagacccagc  2580
agggtggcta gccatggacc cagacagtgg gcaggtcaca gctgtgggca ccctcgaccg  2640
tgaggatgag cagtttgtga ggaacaacat ctatgaagtc atggtcttgg ccatggacaa  2700
tggaagccct cccaccactg gcacgggaac ccttctgcta acactgattg atgtcaatga  2760
ccatggccca gtccctgagc cccgtcagat caccatctgc aaccaaagcc ctgtgcgcca  2820
ggtgctgaac atcacggaca aggacctgtc tccccacacc tccccttttcc aggcccagct  2880
cacagatgac tcagacatct actggacggc agaggtcaac gaggaaggtg acacagtggt  2940
cttgtccctg aagaagttcc tgaagcagga tacatatgac gtgcacccttt ctctgtctga  3000
ccatggcaac aaagagcagc tgacggtgat cagggccact gtgtgcgact gcatggcca  3060
tgtcgaaacc tgccctggac cctggaaggg aggtttcatc ctcccctgtg cctggggctgt  3120
cctggctctg ctgttcctcc tgctggtgct gcttttgttg gtgagaaaga gcggaagat  3180
caaggagccc ctcctactcc agaagatgac acccgtgac aacgtcttct actatggcga  3240
agaggggggt ggcgaagagg accaggacta tgacatcacc cagctccacc gaggtctgga  3300
ggccaggccg gaggtggttc tccgcaatga cgtggcacca accatcatcc cgacacccat  3360
gtaccgtcct cggccagcca acccagatga aatcggcaac tttataattg agaacctgaa  3420
ggcggctaac acagacccca cagccccgcc ctacgacacc ctcttggtgt cgactatga  3480
gggcagcggc tccgacgccg cgtccctgag ctccctcacc cctccgcct ccgaccaaga  3540
ccaagattac gattatctga acgagtgggg cagccgcttc aagaagctgg cagacatgta  3600
cggtggcggg gaggacgact agccggcctg cctgcagggc tggggaccaa acgtcaggcc  3660
acagagcatc tccaagggt ctcagttccc ccttcagctg aggacttcgg agcttgtcag  3720
gaagtggccg tagcaacttg gcggagacag gctatgagtc tgacgttaga gtggtggctt  3780
ccttagcctt tcaggatgga ggaatgtggg cagtttgact tcagcactga aaacctctcc  3840
acctgggcca gggttgcctc agaggccaag ttttccagaag cctcttacct gccgtaaaat  3900
gctcaaccct gtgtcctggg cctgggcctg ctgtgactga cctacagtgg actttctctc  3960
tggaatggaa ccttcttagg cctcctggtg caacttaatt ttttttttta atgctatctt  4020
caaaacgtta gagaaagttc ttcaaaagtg cagcccagag ctgctgggcc cactggccgt  4080
cctgcatttc tggtttccag accccaatgc ctcccattcg gatggatctc tgcgttttta  4140
tactgagtgt gcctaggttg cccttatttt tttattttcc ctgttgcgtt gctatagatg  4200
aagggtgagg acaatcgtgt atatgtacta gaactttttt attaaagaaa cttttcccag  4260
aggtgcctgg ggagtg                                                  4276
```

<210> SEQ ID NO 2
<211> LENGTH: 829
<212> TYPE: PRT
<213> ORGANISM: Homo sapiens

<400> SEQUENCE: 2

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly

```
                35                  40                  45
Gln Ala Leu Gly Lys Val Phe Met Gly Cys Pro Gly Gln Glu Pro Ala
 50                  55                  60

Leu Phe Ser Thr Asp Asn Asp Phe Thr Val Arg Asn Gly Glu Thr
 65                  70                  75                  80

Val Gln Glu Arg Arg Ser Leu Lys Glu Arg Asn Pro Leu Lys Ile Phe
                 85                  90                  95

Pro Ser Lys Arg Ile Leu Arg Arg His Lys Arg Asp Trp Val Val Ala
                100                 105                 110

Pro Ile Ser Val Pro Glu Asn Gly Lys Gly Pro Phe Pro Gln Arg Leu
            115                 120                 125

Asn Gln Leu Lys Ser Asn Lys Asp Arg Asp Thr Lys Ile Phe Tyr Ser
        130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
450                 455                 460
```

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
            485                 490                 495

Ala Val Gly Thr Leu Asp Arg Glu Asp Glu Gln Phe Val Arg Asn Asn
        500                 505                 510

Ile Tyr Glu Val Met Val Leu Ala Met Asp Asn Gly Ser Pro Pro Thr
    515                 520                 525

Thr Gly Thr Gly Thr Leu Leu Leu Thr Leu Ile Asp Val Asn Asp His
530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
    610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
    690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825

<210> SEQ ID NO 3
<211> LENGTH: 348
<212> TYPE: DNA
<213> ORGANISM: Mus musculus

<400> SEQUENCE: 3
caggtccaac tgcagcagcc tggggctgaa ctggtgaggc ctgggtcttc agtgaagctg      60

-continued

```
tcctgcaagg cttctggcta caccttcacc agtttctgga tacattgggt gaagcagagg    120
cctatgcaag gccttgaatg gattggtaac attgaccctt ctgacagtga aactcactac    180
aatcaatatt tcaaggacag ggccacattg actgtagaca ggtcttccag cacagcctac    240
atgcacctca ccagcctgac atctgaggac tctgcggtct attactgtgc aagaggtggg    300
acagggtttt cttcctgggg ccaagggact ctggtcactg tctctgca                 348
```

```
<210> SEQ ID NO 4
<211> LENGTH: 116
<212> TYPE: PRT
<213> ORGANISM: Homo sapiens

<400> SEQUENCE: 4
```

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Phe
            20                  25                  30

Trp Ile His Trp Val Lys Gln Arg Pro Met Gln Gly Leu Glu Trp Ile
        35                  40                  45

Gly Asn Ile Asp Pro Ser Asp Ser Glu Thr His Tyr Asn Gln Tyr Phe
    50                  55                  60

Lys Asp Arg Ala Thr Leu Thr Val Asp Arg Ser Ser Ser Thr Ala Tyr
65                  70                  75                  80

Met His Leu Thr Ser Leu Thr Ser Glu Asp Ser Ala Val Tyr Tyr Cys
                85                  90                  95

Ala Arg Gly Gly Thr Gly Phe Ser Ser Trp Gly Gln Gly Thr Leu Val
            100                 105                 110

Thr Val Ser Ala
        115

```
<210> SEQ ID NO 5
<211> LENGTH: 15
<212> TYPE: DNA
<213> ORGANISM: Mus musculus

<400> SEQUENCE: 5
agtttctgga tacat                                                      15

<210> SEQ ID NO 6
<211> LENGTH: 5
<212> TYPE: PRT
<213> ORGANISM: Mus musculus

<400> SEQUENCE: 6
```

Ser Phe Trp Ile His
1               5

```
<210> SEQ ID NO 7
<211> LENGTH: 51
<212> TYPE: DNA
<213> ORGANISM: Mus musculus

<400> SEQUENCE: 7
aacattgacc cttctgacag tgaaactcac tacaatcaat atttcaagga c              51

<210> SEQ ID NO 8
<211> LENGTH: 17
<212> TYPE: PRT
<213> ORGANISM: Mus musculus
```

```
<400> SEQUENCE: 8

Asn Ile Asp Pro Ser Asp Ser Glu Thr His Tyr Asn Gln Tyr Phe Lys
1               5                   10                  15

Asp

<210> SEQ ID NO 9
<211> LENGTH: 21
<212> TYPE: DNA
<213> ORGANISM: Mus musculus

<400> SEQUENCE: 9
ggtgggacag ggtttcttc c                                              21

<210> SEQ ID NO 10
<211> LENGTH: 7
<212> TYPE: PRT
<213> ORGANISM: Mus musculus

<400> SEQUENCE: 10

Gly Gly Thr Gly Phe Ser Ser
1               5

<210> SEQ ID NO 11
<211> LENGTH: 321
<212> TYPE: DNA
<213> ORGANISM: Mus musculus

<400> SEQUENCE: 11
gacatcaaaa tgacccagtc tccatcttcc atgtatgcat ctctaggaga gagagtcact      60
atcacttgca aggcgagtca ggacattgat agctatttaa gctggttcca gcagaaacct     120
gggaaatctc ctaagaccct gatccatcgt gcaaatagat tggtagatgg ggtcccatca     180
aggttcagtg gcagtggatc tgggcaagat tattctctca ccatcagtag cctggaatat     240
gaagatatgg gaatctatta ttgtctacag tatgatgagt ttcctcggac gttcggtgga     300
ggcaccaagc tggaaatcaa a                                              321

<210> SEQ ID NO 12
<211> LENGTH: 107
<212> TYPE: PRT
<213> ORGANISM: Mus musculus

<400> SEQUENCE: 12

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asp Ser Tyr
            20                  25                  30

Leu Ser Trp Phe Gln Gln Lys Pro Gly Lys Ser Pro Lys Thr Leu Ile
        35                  40                  45

His Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105
```

```
<210> SEQ ID NO 13
<211> LENGTH: 33
<212> TYPE: DNA
<213> ORGANISM: Mus musculus

<400> SEQUENCE: 13
aaggcgagtc aggacattga tagctattta agc                                 33

<210> SEQ ID NO 14
<211> LENGTH: 11
<212> TYPE: PRT
<213> ORGANISM: Mus musculus

<400> SEQUENCE: 14

Lys Ala Ser Gln Asp Ile Asp Ser Tyr Leu Ser
 1               5                  10

<210> SEQ ID NO 15
<211> LENGTH: 21
<212> TYPE: DNA
<213> ORGANISM: Mus musculus

<400> SEQUENCE: 15
cgtgcaaata gattggtaga t                                              21

<210> SEQ ID NO 16
<211> LENGTH: 7
<212> TYPE: PRT
<213> ORGANISM: Mus musculus

<400> SEQUENCE: 16

Arg Ala Asn Arg Leu Val Asp
 1               5

<210> SEQ ID NO 17
<211> LENGTH: 27
<212> TYPE: DNA
<213> ORGANISM: Mus musculus

<400> SEQUENCE: 17
ctacagtatg atgagtttcc tcggacg                                        27

<210> SEQ ID NO 18
<211> LENGTH: 9
<212> TYPE: PRT
<213> ORGANISM: Mus musculus

<400> SEQUENCE: 18

Leu Gln Tyr Asp Glu Phe Pro Arg Thr
 1               5

<210> SEQ ID NO 19
<211> LENGTH: 348
<212> TYPE: DNA
<213> ORGANISM: Mus musculus

<400> SEQUENCE: 19
ctggtccaac tccagcagcc tggggctgaa ctggtgaggc ctgggtcttc agtgaagctg    60
tcctgcaaga cctctggcta caccttcacc agctactgga tgcattggat aaagcagagg   120
cctatacaag gccttgaatg gattggtaac attgaccctt ctgatagtga aactcactac   180
aatcaaaact tcaatgacag ggccacattc accgtagaca atcctccag cacagcctac    240 atggaactca gcagcctgac atctgaggac tctgcggtct attactgtgc aagaggtggg   300
```

```
acaggcttcg cttactgggg ccaagggact ctggtcactg tctctgca                    348
```

<210> SEQ ID NO 20
<211> LENGTH: 116
<212> TYPE: PRT
<213> ORGANISM: Mus musculus

<400> SEQUENCE: 20

Leu Val Gln Leu Gln Gln Pro Gly Ala Glu Leu Val Arg Pro Gly Ser
1               5                   10                  15

Ser Val Lys Leu Ser Cys Lys Thr Ser Gly Tyr Thr Phe Thr Ser Tyr
            20                  25                  30

Trp Met His Trp Ile Lys Gln Arg Pro Ile Gln Gly Leu Glu Trp Ile
        35                  40                  45

Gly Asn Ile Asp Pro Ser Asp Ser Glu Thr His Tyr Asn Gln Asn Phe
    50                  55                  60

Asn Asp Arg Ala Thr Phe Thr Val Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Gly Thr Gly Phe Ala Tyr Trp Gly Gln Gly Thr Leu Val
            100                 105                 110

Thr Val Ser Ala
        115

<210> SEQ ID NO 21
<211> LENGTH: 15
<212> TYPE: DNA
<213> ORGANISM: Mus musculus

<400> SEQUENCE: 21

```
agctactgga tgcat                                                        15
```

<210> SEQ ID NO 22
<211> LENGTH: 5
<212> TYPE: PRT
<213> ORGANISM: Mus musculus

<400> SEQUENCE: 22

Ser Tyr Trp Met His
1               5

<210> SEQ ID NO 23
<211> LENGTH: 51
<212> TYPE: DNA
<213> ORGANISM: Mus musculus

<400> SEQUENCE: 23

```
aacattgacc cttctgatag tgaaactcac tacaatcaaa acttcaatga c                51
```

<210> SEQ ID NO 24
<211> LENGTH: 17
<212> TYPE: PRT
<213> ORGANISM: Mus musculus

<400> SEQUENCE: 24

Asn Ile Asp Pro Ser Asp Ser Glu Thr His Tyr Asn Gln Asn Phe Asn
1               5                   10                  15

Asp

<210> SEQ ID NO 25
<211> LENGTH: 21
<212> TYPE: DNA
<213> ORGANISM: Mus musculus

<400> SEQUENCE: 25
ggtgggacag gcttcgctta c                                              21

<210> SEQ ID NO 26
<211> LENGTH: 7
<212> TYPE: PRT
<213> ORGANISM: Mus musculus

<400> SEQUENCE: 26

Gly Gly Thr Gly Phe Ala Tyr
1               5

<210> SEQ ID NO 27
<211> LENGTH: 321
<212> TYPE: DNA
<213> ORGANISM: Mus musculus

<400> SEQUENCE: 27
gacatcaaga tgacccagtc tccctcttcc atgtatgcat ctctaggaga gagagtcact      60
atcacttgca aggcgagtca ggacattaat aactatttag ctggttcca acagaaacca     120 ggtaaatctc ctaagaccct gatccatcga acagatagat tgatagaagg ggtcccatca    180
aggttcagtg gcagtggatc tgggcaggat tattctctca ccatcagcag cctggaatat    240
gaagatgtgg gaacttatta ttgtctacag tatgatgagt ttcctcggat gttcggtgga    300
ggcaccaagc tggaaatcaa a                                             321

<210> SEQ ID NO 28
<211> LENGTH: 107
<212> TYPE: PRT
<213> ORGANISM: Mus musculus

<400> SEQUENCE: 28

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Gly Trp Phe Gln Gln Lys Pro Gly Lys Ser Pro Lys Thr Leu Ile
        35                  40                  45

His Arg Thr Asp Arg Leu Ile Glu Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Val Gly Thr Tyr Tyr Cys Leu Gln Tyr Asp Glu Phe Pro Arg
                85                  90                  95

Met Phe Gly Gly Gly Thr Lys Leu Glu Ile Lys
            100                 105

<210> SEQ ID NO 29
<211> LENGTH: 33
<212> TYPE: DNA
<213> ORGANISM: Mus musculus

<400> SEQUENCE: 29
aaggcgagtc aggacattaa taactatttta ggc                                33

-continued

<210> SEQ ID NO 30
<211> LENGTH: 11
<212> TYPE: PRT
<213> ORGANISM: Mus musculus

<400> SEQUENCE: 30

Lys Ala Ser Gln Asp Ile Asn Asn Tyr Leu Gly
1               5                   10

<210> SEQ ID NO 31
<211> LENGTH: 21
<212> TYPE: DNA
<213> ORGANISM: Mus musculus

<400> SEQUENCE: 31
cgaacagata gattgataga a                                         21

<210> SEQ ID NO 32
<211> LENGTH: 7
<212> TYPE: PRT
<213> ORGANISM: Mus musculus

<400> SEQUENCE: 32

Arg Thr Asp Arg Leu Ile Glu
1               5

<210> SEQ ID NO 33
<211> LENGTH: 27
<212> TYPE: DNA
<213> ORGANISM: Mus musculus

<400> SEQUENCE: 33
ctacagtatg atgagtttcc tcggatg                                   27

<210> SEQ ID NO 34
<211> LENGTH: 9
<212> TYPE: PRT
<213> ORGANISM: Mus musculus

<400> SEQUENCE: 34

Leu Gln Tyr Asp Glu Phe Pro Arg Met
1               5

<210> SEQ ID NO 35
<211> LENGTH: 348
<212> TYPE: DNA
<213> ORGANISM: Mus musculus

<400> SEQUENCE: 35
ctggtccaac tccagcagcc tggggctgaa ctggtgaggc ctgggtcttc agtgaagctg      60
tcctgcaagg cttctggcta caccttcacc agctactgga tgcattggat aaagcagagg     120
cctatacaag gccttgaatg gattggaaac attgaccctt ctgatagtga aactcactac     180
aatcaaaagt tcaatgacag ggccagatta actgtagaca atcctccag cacagcctac      240 atgcacctca gcagcctgac atctgaggac tctgcggtct attactgtgc aagaggtggg     300
acaggatttg cttactgggg ccaagggact ctggtcactg tctctgca                 348

<210> SEQ ID NO 36
<211> LENGTH: 116
<212> TYPE: PRT
<213> ORGANISM: Mus musculus

<400> SEQUENCE: 36

Leu Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Met His Trp Ile Lys Gln Arg Pro Ile Gln Gly Leu Glu Trp Ile
        35                  40                  45

Gly Asn Ile Asp Pro Ser Asp Ser Glu Thr His Tyr Asn Gln Lys Phe
    50                  55                  60

Asn Asp Arg Ala Arg Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
            85                  90                  95

Ala Arg Gly Gly Thr Gly Phe Ala Tyr Trp Gly Gln Gly Thr Leu Val
            100                 105                 110

Thr Val Ser Ala
        115

<210> SEQ ID NO 37
<211> LENGTH: 15
<212> TYPE: DNA
<213> ORGANISM: Mus musculus

<400> SEQUENCE: 37
agctactgga tgcat                                                  15

<210> SEQ ID NO 38
<211> LENGTH: 5
<212> TYPE: PRT
<213> ORGANISM: Mus musculus

<400> SEQUENCE: 38

Ser Tyr Trp Met His
1               5

<210> SEQ ID NO 39
<211> LENGTH: 57
<212> TYPE: DNA
<213> ORGANISM: Mus musculus

<400> SEQUENCE: 39
aacattgacc cttctgatag tgaaactcac tacaatcaaa agttcaatga cagggcc    57

<210> SEQ ID NO 40
<211> LENGTH: 19
<212> TYPE: PRT
<213> ORGANISM: Mus musculus

<400> SEQUENCE: 40

Asn Ile Asp Pro Ser Asp Ser Glu Thr His Tyr Asn Gln Lys Phe Asn
1               5                   10                  15

Asp Arg Ala

<210> SEQ ID NO 41
<211> LENGTH: 21
<212> TYPE: DNA
<213> ORGANISM: Mus musculus

<400> SEQUENCE: 41
ggtgggacag gatttgctta c                                                    21

<210> SEQ ID NO 42
<211> LENGTH: 7
<212> TYPE: PRT
<213> ORGANISM: Mus musculus

<400> SEQUENCE: 42

Gly Gly Thr Gly Phe Ala Tyr
1               5

<210> SEQ ID NO 43
<211> LENGTH: 321
<212> TYPE: DNA
<213> ORGANISM: Mus musculus

<400> SEQUENCE: 43
gacatcaaga tgacccagtc tccctcttcc atgtatgcat ctctaggaga gagagtcact    60
atcacttgca aggcgagtca ggacattaat aactatttag ctggttcca acagaaacca   120 ggtaaatctc ctaagaccct gatccatcgt acagatagat tgatagaagg ggtcccatca   180
cggttcagtg gcagtggatc tgggcaggat tattctctca ccatcagcag cctggaatat   240
gaagatgtgg gaacttatta ttgtctacag tatgatgagt ttcctcggat gttcggtgga   300
ggcaccaagc tggacatcaa a                                             321

<210> SEQ ID NO 44
<211> LENGTH: 107
<212> TYPE: PRT
<213> ORGANISM: Mus musculus

<400> SEQUENCE: 44

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Gly Trp Phe Gln Gln Lys Pro Gly Lys Ser Pro Lys Thr Leu Ile
        35                  40                  45

His Arg Thr Asp Arg Leu Ile Glu Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Val Gly Thr Tyr Tyr Cys Leu Gln Tyr Asp Glu Phe Pro Arg
                85                  90                  95

Met Phe Gly Gly Gly Thr Lys Leu Asp Ile Lys
            100                 105

<210> SEQ ID NO 45
<211> LENGTH: 33
<212> TYPE: DNA
<213> ORGANISM: Mus musculus

<400> SEQUENCE: 45
aaggcgagtc aggacattaa taactattta ggc                                33

<210> SEQ ID NO 46
<211> LENGTH: 11
<212> TYPE: PRT
<213> ORGANISM: Mus musculus

<400> SEQUENCE: 46

Lys Ala Ser Gln Asp Ile Asn Asn Tyr Leu Gly
1               5                   10

<210> SEQ ID NO 47
<211> LENGTH: 21
<212> TYPE: DNA
<213> ORGANISM: Mus musculus

<400> SEQUENCE: 47
cgtacagata gattgataga a                                              21

<210> SEQ ID NO 48
<211> LENGTH: 7
<212> TYPE: PRT
<213> ORGANISM: Mus musculus

<400> SEQUENCE: 48

Arg Thr Asp Arg Leu Ile Glu
1               5

<210> SEQ ID NO 49
<211> LENGTH: 27
<212> TYPE: DNA
<213> ORGANISM: Mus musculus

<400> SEQUENCE: 49
ctacagtatg atgagtttcc tcggatg                                        27

<210> SEQ ID NO 50
<211> LENGTH: 9
<212> TYPE: PRT
<213> ORGANISM: Mus musculus

<400> SEQUENCE: 50

Leu Gln Tyr Asp Glu Phe Pro Arg Met
1               5

<210> SEQ ID NO 51
<211> LENGTH: 354
<212> TYPE: DNA
<213> ORGANISM: Mus musculus

<400> SEQUENCE: 51
caggtccaac tgcagcagcc tggggctgaa ctggtcaagc ctgggacttc agtgaagctg     60
tcctgcaagt cttctggata caccttcact agctattgga tacactgggt gaaacagagg   120
cctggacatg gccttgagtg gatcggagag attgatcctt ctgataatta tacttactat   180
aatcaaaatt tcaagggcaa ggccacattg actatagaca atcctccag cacagcctac    240 atgcaactca acagcctgac atctgaggac tctgcggtct tttactgtgc aagatcgggc   300
tatggtaact tgtttgttta ttggggccaa gggactctgg tcactgtctc tgca          354

<210> SEQ ID NO 52
<211> LENGTH: 118
<212> TYPE: PRT
<213> ORGANISM: Mus musculus

<400> SEQUENCE: 52

Gln Val Gln Leu Gln Gln Pro Gly Ala Glu Leu Val Lys Pro Gly Thr
1               5                   10                  15

Ser Val Lys Leu Ser Cys Lys Ser Ser Gly Tyr Thr Phe Thr Ser Tyr
            20                  25                  30

Trp Ile His Trp Val Lys Gln Arg Pro Gly His Gly Leu Glu Trp Ile
          35                  40                  45

Gly Glu Ile Asp Pro Ser Asp Asn Tyr Thr Tyr Tyr Asn Gln Asn Phe
     50                  55                  60

Lys Gly Lys Ala Thr Leu Thr Ile Asp Lys Ser Ser Thr Ala Tyr
65                  70                  75                  80

Met Gln Leu Asn Ser Leu Thr Ser Glu Asp Ser Ala Val Phe Tyr Cys
              85                  90                  95

Ala Arg Ser Gly Tyr Gly Asn Leu Phe Val Tyr Trp Gly Gln Gly Thr
             100                 105                 110

Leu Val Thr Val Ser Ala
         115

<210> SEQ ID NO 53
<211> LENGTH: 15
<212> TYPE: DNA
<213> ORGANISM: Mus musculus

<400> SEQUENCE: 53
agctattgga tacac                                                            15

<210> SEQ ID NO 54
<211> LENGTH: 5
<212> TYPE: PRT
<213> ORGANISM: Mus musculus

<400> SEQUENCE: 54

Ser Tyr Trp Ile His
1               5

<210> SEQ ID NO 55
<211> LENGTH: 51
<212> TYPE: DNA
<213> ORGANISM: Mus musculus

<400> SEQUENCE: 55
gagattgatc cttctgataa ttatacttac tataatcaaa atttcaaggg c                    51

<210> SEQ ID NO 56
<211> LENGTH: 17
<212> TYPE: PRT
<213> ORGANISM: Mus musculus

<400> SEQUENCE: 56

Glu Ile Asp Pro Ser Asp Asn Tyr Thr Tyr Tyr Asn Gln Asn Phe Lys
1               5                   10                  15

Gly

<210> SEQ ID NO 57
<211> LENGTH: 27
<212> TYPE: DNA
<213> ORGANISM: Mus musculus

<400> SEQUENCE: 57
tcgggctatg gtaacttgtt tgtttat                                               27

<210> SEQ ID NO 58
<211> LENGTH: 9
<212> TYPE: PRT
<213> ORGANISM: Mus musculus

<400> SEQUENCE: 58

Ser Gly Tyr Gly Asn Leu Phe Val Tyr
1               5

<210> SEQ ID NO 59
<211> LENGTH: 318
<212> TYPE: DNA
<213> ORGANISM: Mus musculus

<400> SEQUENCE: 59
caaattgttc tcacccagtc tccagcaatc atgtcttcat ctccagggga gaaggtcacc    60
atgtcctgca gtgccacctc aagtgttact tacatgtact ggtaccagca gaagccagga   120
tcctccccca aaccctggat ttttcgcaca tccaacctgg cttctggagt ccctactcgc   180
ttcagtggca gtgggtctgg gacctcttac tctctcacga tcagcagcat ggaggctgaa   240
gatgctgcca cttattactg ccagcactat catatttacc cacgacgtt cggtggaggc    300 accaagctgg aaatcaaa                                                 318

<210> SEQ ID NO 60
<211> LENGTH: 106
<212> TYPE: PRT
<213> ORGANISM: Mus musculus

<400> SEQUENCE: 60

Gln Ile Val Leu Thr Gln Ser Pro Ala Ile Met Ser Ser Ser Pro Gly
1               5                   10                  15

Glu Lys Val Thr Met Ser Cys Ser Ala Thr Ser Ser Val Thr Tyr Met
            20                  25                  30

Tyr Trp Tyr Gln Gln Lys Pro Gly Ser Ser Pro Lys Pro Trp Ile Phe
        35                  40                  45

Arg Thr Ser Asn Leu Ala Ser Gly Val Pro Thr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Tyr His Ile Tyr Pro Arg Thr
                85                  90                  95

Phe Gly Gly Gly Thr Lys Leu Glu Ile Lys
            100                 105

<210> SEQ ID NO 61
<211> LENGTH: 30
<212> TYPE: DNA
<213> ORGANISM: Mus musculus

<400> SEQUENCE: 61
agtgccacct caagtgttac ttacatgtac                                     30

<210> SEQ ID NO 62
<211> LENGTH: 10
<212> TYPE: PRT
<213> ORGANISM: Mus musculus

<400> SEQUENCE: 62

Ser Ala Thr Ser Ser Val Thr Tyr Met Tyr
1               5                   10

<210> SEQ ID NO 63
<211> LENGTH: 21
<212> TYPE: DNA

<213> ORGANISM: Mus musculus

<400> SEQUENCE: 63
cgcacatcca acctggcttc t    21

<210> SEQ ID NO 64
<211> LENGTH: 7
<212> TYPE: PRT
<213> ORGANISM: Mus musculus

<400> SEQUENCE: 64

Arg Thr Ser Asn Leu Ala Ser
1               5

<210> SEQ ID NO 65
<211> LENGTH: 27
<212> TYPE: DNA
<213> ORGANISM: Mus musculus

<400> SEQUENCE: 65
cagcactatc atatttaccc acggacg    27

<210> SEQ ID NO 66
<211> LENGTH: 9
<212> TYPE: PRT
<213> ORGANISM: Mus musculus

<400> SEQUENCE: 66

Gln His Tyr His Ile Tyr Pro Arg Thr
1               5

<210> SEQ ID NO 67
<211> LENGTH: 354
<212> TYPE: DNA
<213> ORGANISM: Mus musculus

<400> SEQUENCE: 67
caggtccaac tgcagcagcc tggggctgaa ctggtcaagc ctggggcttc agtgaagctg    60
tcctgcaagt cttctggata caccttcact agctattgga tacactgggt gaaacagagg   120
cctggacatg gccttgagtg gatcggagag attgatcctt ctgattccta cttactat    180
aatcaaaatt tcaagggcaa ggccacattg actatagaca atcctccag cacagcctac   240
atgcaactca acagcctgac atctgaggac tctgcggtct tttactgtgc aagatcgggc   300
tatggtaact tgtttgtta ttggggccaa gggactctgg tcactgtctc tgca          354

<210> SEQ ID NO 68
<211> LENGTH: 118
<212> TYPE: PRT
<213> ORGANISM: Mus musculus

<400> SEQUENCE: 68

Gln Val Gln Leu Gln Gln Pro Gly Ala Glu Leu Val Lys Pro Gly Thr
1               5                   10                  15

Ser Val Lys Leu Ser Cys Lys Ser Ser Gly Tyr Thr Phe Thr Ser Tyr
            20                  25                  30

Trp Ile His Trp Val Lys Gln Arg Pro Gly His Gly Leu Glu Trp Ile
        35                  40                  45

Gly Glu Ile Asp Pro Ser Asp Ser Tyr Thr Tyr Asn Gln Asn Phe
    50                  55                  60

Lys Gly Lys Ala Thr Leu Thr Ile Asp Lys Ser Ser Ser Thr Ala Tyr

```
                65                  70                  75                  80
Met Gln Leu Asn Ser Leu Thr Ser Glu Asp Ser Ala Val Phe Tyr Cys
                    85                  90                  95

Ala Arg Ser Gly Tyr Gly Asn Leu Phe Val Tyr Trp Gly Gln Gly Thr
                    100                 105                 110

Leu Val Thr Val Ser Ala
        115

<210> SEQ ID NO 69
<211> LENGTH: 51
<212> TYPE: DNA
<213> ORGANISM: Mus musculus

<400> SEQUENCE: 69
gagattgatc cttctgattc ctatacttac tataatcaaa atttcaaggg c          51

<210> SEQ ID NO 70
<211> LENGTH: 17
<212> TYPE: PRT
<213> ORGANISM: Mus musculus

<400> SEQUENCE: 70

Glu Ile Asp Pro Ser Asp Ser Tyr Thr Tyr Tyr Asn Gln Asn Phe Lys
1               5                   10                  15
Gly

<210> SEQ ID NO 71
<211> LENGTH: 354
<212> TYPE: DNA
<213> ORGANISM: Mus musculus

<400> SEQUENCE: 71
caggtccaac tgcagcagcc tggggctgaa ctggtcaagc ctggacttc agtgaagctg     60
tcctgcaagt cttctggata caccttcact agctattgga tacactgggt gaaacagagg    120
cctggacatg gccttgagtg gatcggagag attgatcctt ctgataccta tacttactat   180
aatcaaaatt tcaagggcaa ggccacattg actatagaca atcctccag cacagcctac    240
atgcaactca cagcctgac atctgaggac tctgcggtct tttactgtgc aagatcgggc    300
tatggtaact gtttgtttta ttggggccaa gggactctgg tcactgtctc tgca         354

<210> SEQ ID NO 72
<211> LENGTH: 118
<212> TYPE: PRT
<213> ORGANISM: Mus musculus

<400> SEQUENCE: 72

Gln Val Gln Leu Gln Gln Pro Gly Ala Glu Leu Val Lys Pro Gly Thr
1               5                   10                  15

Ser Val Lys Leu Ser Cys Lys Ser Ser Gly Tyr Thr Phe Thr Ser Tyr
                20                  25                  30

Trp Ile His Trp Val Lys Gln Arg Pro Gly His Gly Leu Glu Trp Ile
            35                  40                  45

Gly Glu Ile Asp Pro Ser Asp Ser Tyr Thr Tyr Tyr Asn Gln Asn Phe
        50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Phe Tyr Cys
                85                  90                  95
```

Ala Arg Ser Gly Tyr Gly Asn Leu Phe Val Tyr Trp Gly Gln Gly Thr
            100                 105                 110

Leu Val Thr Val Ser Ala
        115

<210> SEQ ID NO 73
<211> LENGTH: 51
<212> TYPE: DNA
<213> ORGANISM: Mus musculus

<400> SEQUENCE: 73
gagattgatc cttctgatac ctatacttac tataatcaaa atttcaaggg c         51

<210> SEQ ID NO 74
<211> LENGTH: 17
<212> TYPE: PRT
<213> ORGANISM: Mus musculus

<400> SEQUENCE: 74

Glu Ile Asp Pro Ser Asp Thr Tyr Thr Tyr Tyr Asn Gln Asn Phe Lys
1               5                   10                  15

Gly

<210> SEQ ID NO 75
<211> LENGTH: 354
<212> TYPE: DNA
<213> ORGANISM: Mus musculus

<400> SEQUENCE: 75
caggtccaac tgcagcagcc tggggctgaa ctggtcaagc ctgggacttc agtgaagctg      60
tcctgcaagt cttctggata caccttcact agctattgga tacactgggt gaaacagagg     120
cctggacatg gccttgagtg gatcggagag attgatcctt ctgatgccta tacttactat     180
aatcaaaatt tcaagggcaa ggccacattg actatagaca atcctccag cacagcctac      240 atgcaactca acagcctgac atctgaggac tctgcggtct tttactgtgc aagatcgggc     300
tatggtaact tgtttgttta ttggggccaa gggactctgg tcactgtctc tgca           354

<210> SEQ ID NO 76
<211> LENGTH: 118
<212> TYPE: PRT
<213> ORGANISM: Mus musculus

<400> SEQUENCE: 76

Gln Val Gln Leu Gln Gln Pro Gly Ala Glu Leu Val Lys Pro Gly Thr
1               5                   10                  15

Ser Val Lys Leu Ser Cys Lys Ser Ser Gly Tyr Thr Phe Thr Ser Tyr
            20                  25                  30

Trp Ile His Trp Val Lys Gln Arg Pro Gly His Gly Leu Glu Trp Ile
        35                  40                  45

Gly Glu Ile Asp Pro Ser Asp Ala Tyr Thr Tyr Tyr Asn Gln Asn Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Phe Tyr Cys
                85                  90                  95

Ala Arg Ser Gly Tyr Gly Asn Leu Phe Val Tyr Trp Gly Gln Gly Thr
            100                 105                 110

Leu Val Thr Val Ser Ala
        115

<210> SEQ ID NO 77
<211> LENGTH: 51
<212> TYPE: DNA
<213> ORGANISM: Mus musculus

<400> SEQUENCE: 77
gagattgatc cttctgatgc ctatacttac tataatcaaa atttcaaggg c          51

<210> SEQ ID NO 78
<211> LENGTH: 17
<212> TYPE: PRT
<213> ORGANISM: Mus musculus

<400> SEQUENCE: 78

Glu Ile Asp Pro Ser Asp Ala Tyr Thr Tyr Tyr Asn Gln Asn Phe Lys
1               5                   10                  15

Gly

<210> SEQ ID NO 79
<211> LENGTH: 354
<212> TYPE: DNA
<213> ORGANISM: Mus musculus

<400> SEQUENCE: 79
caggtccaac tgcagcagcc tggggctgaa ctggtcaagc ctgggacttc agtgaagctg      60
tcctgcaagt cttctggata caccttcact agctattgga tacactgggt gaaacagagg     120
cctggacatg gccttgagtg gatcggagag attgatcctt ctgatcagta tacttactat     180
aatcaaaatt tcaagggcaa ggccacattg actatagaca atcctccag cacagcctac      240 atgcaactca acagcctgac atctgaggac tctgcggtct tttactgtgc aagatcgggc     300
tatggtaact tgtttgttta ttggggccaa gggactctgg tcactgtctc tgca           354

<210> SEQ ID NO 80
<211> LENGTH: 118
<212> TYPE: PRT
<213> ORGANISM: Mus musculus

<400> SEQUENCE: 80

Gln Val Gln Leu Gln Gln Pro Gly Ala Glu Leu Val Lys Pro Gly Thr
1               5                   10                  15

Ser Val Lys Leu Ser Cys Lys Ser Ser Gly Tyr Thr Phe Thr Ser Tyr
            20                  25                  30

Trp Ile His Trp Val Lys Gln Arg Pro Gly His Gly Leu Glu Trp Ile
        35                  40                  45

Gly Glu Ile Asp Pro Ser Asp Gln Tyr Thr Tyr Tyr Asn Gln Asn Phe
    50                  55                  60

Lys Gly Lys Ala Thr Leu Thr Ile Asp Lys Ser Ser Thr Ala Tyr
65                  70                  75                  80

Met Gln Leu Asn Ser Leu Thr Ser Glu Asp Ser Ala Val Phe Tyr Cys
                85                  90                  95

Ala Arg Ser Gly Tyr Gly Asn Leu Phe Val Tyr Trp Gly Gln Gly Thr
            100                 105                 110

Leu Val Thr Val Ser Ala
        115

-continued

<210> SEQ ID NO 81
<211> LENGTH: 51
<212> TYPE: DNA
<213> ORGANISM: Mus musculus

<400> SEQUENCE: 81
gagattgatc cttctgatca gtatacttac tataatcaaa atttcaaggg c    51

<210> SEQ ID NO 82
<211> LENGTH: 17
<212> TYPE: PRT
<213> ORGANISM: Mus musculus

<400> SEQUENCE: 82

Glu Ile Asp Pro Ser Asp Gln Tyr Thr Tyr Tyr Asn Gln Asn Phe Lys
1               5                   10                  15
Gly

<210> SEQ ID NO 83
<211> LENGTH: 654
<212> TYPE: PRT
<213> ORGANISM: Homo sapiens

<400> SEQUENCE: 83

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
                20                  25                  30

Glu Ala Glu Val Thr Leu Glu Ala Gly Ala Glu Gln Glu Pro Gly
            35                  40                  45

Gln Ala Leu Gly Lys Val Phe Met Gly Cys Pro Gly Gln Glu Pro Ala
        50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile

```
                260                 265                 270
His Arg Ser Thr Gly Thr Ile Ser Val Ile Ser Ser Gly Leu Asp Arg
            275                 280                 285
Glu Lys Val Pro Glu Tyr Thr Leu Thr Ile Gln Ala Thr Asp Met Asp
            290                 295                 300
Gly Asp Gly Ser Thr Thr Thr Ala Val Ala Val Val Glu Ile Leu Asp
305                 310                 315                 320
Ala Asn Asp Asn Ala Pro Met Phe Asp Pro Gln Lys Tyr Glu Ala His
                325                 330                 335
Val Pro Glu Asn Ala Val Gly His Glu Val Gln Arg Leu Thr Val Thr
                340                 345                 350
Asp Leu Asp Ala Pro Asn Ser Pro Ala Trp Arg Ala Thr Tyr Leu Ile
                355                 360                 365
Met Gly Gly Asp Asp Gly Asp His Phe Thr Ile Thr Thr His Pro Glu
            370                 375                 380
Ser Asn Gln Gly Ile Leu Thr Thr Arg Lys Gly Leu Asp Phe Glu Ala
385                 390                 395                 400
Lys Asn Gln His Thr Leu Tyr Val Glu Val Thr Asn Glu Ala Pro Phe
                405                 410                 415
Val Leu Lys Leu Pro Thr Ser Thr Ala Thr Ile Val Val His Val Glu
                420                 425                 430
Asp Val Asn Glu Ala Pro Val Phe Val Pro Pro Ser Lys Val Val Glu
                435                 440                 445
Val Gln Glu Gly Ile Pro Thr Gly Glu Pro Val Cys Val Tyr Thr Ala
            450                 455                 460
Glu Asp Pro Asp Lys Glu Asn Gln Lys Ile Ser Tyr Arg Ile Leu Arg
465                 470                 475                 480
Asp Pro Ala Gly Trp Leu Ala Met Asp Pro Asp Ser Gly Gln Val Thr
                485                 490                 495
Ala Val Gly Thr Leu Asp Arg Glu Asp Glu Gln Phe Val Arg Asn Asn
            500                 505                 510
Ile Tyr Glu Val Met Val Leu Ala Met Asp Asn Gly Ser Pro Pro Thr
            515                 520                 525
Thr Gly Thr Gly Thr Leu Leu Leu Thr Leu Ile Asp Val Asn Asp His
            530                 535                 540
Gly Pro Val Pro Glu Pro Arg Gln Ile Thr Ile Cys Asn Gln Ser Pro
545                 550                 555                 560
Val Arg Gln Val Leu Asn Ile Thr Asp Lys Asp Leu Ser Pro His Thr
                565                 570                 575
Ser Pro Phe Gln Ala Gln Leu Thr Asp Ser Asp Ile Tyr Trp Thr
            580                 585                 590
Ala Glu Val Asn Glu Glu Gly Asp Thr Val Val Leu Ser Leu Lys Lys
            595                 600                 605
Phe Leu Lys Gln Asp Thr Tyr Asp Val His Leu Ser Leu Ser Asp His
            610                 615                 620
Gly Asn Lys Glu Gln Leu Thr Val Ile Arg Ala Thr Val Cys Asp Cys
625                 630                 635                 640
His Gly His Val Glu Thr Cys Pro Gly Pro Trp Lys Gly Gly
                645                 650

<210> SEQ ID NO 84
<211> LENGTH: 34
<212> TYPE: DNA
<213> ORGANISM: Artificial
```

```
<220> FEATURE:
<223> OTHER INFORMATION: An artificially synthesized 5' primer sequence
      for VH

<400> SEQUENCE: 84
gggaattcat graatgsasc tgggtywtyc tctt                                  34

<210> SEQ ID NO 85
<211> LENGTH: 42
<212> TYPE: DNA
<213> ORGANISM: Artificial
<220> FEATURE:
<223> OTHER INFORMATION: An artificially synthesized 5' primer sequence
      for VL
<220> FEATURE:
<221> NAME/KEY: misc_feature
<222> LOCATION: (37)..(37)
<223> OTHER INFORMATION: n is a, c, g, or t

<400> SEQUENCE: 85
actagtcgac atgaggrccc ctgctcagwt tyttggnwtc tt                         42

<210> SEQ ID NO 86
<211> LENGTH: 41
<212> TYPE: DNA
<213> ORGANISM: Artificial
<220> FEATURE:
<223> OTHER INFORMATION: An artificially synthesized 5' primer sequence
      for VL

<400> SEQUENCE: 86
actagtcgac atgggcwtca agatgragtc acakwyycwg g                          41

<210> SEQ ID NO 87
<211> LENGTH: 35
<212> TYPE: DNA
<213> ORGANISM: Artificial
<220> FEATURE:
<223> OTHER INFORMATION: An artificially synthesized 3' primer sequence
      for VH
<220> FEATURE:
<221> NAME/KEY: misc_feature
<222> LOCATION: (30)..(30)
<223> OTHER INFORMATION: n is a, c, g, or t

<400> SEQUENCE: 87
cccaagcttc cagggrccar kggataracn grtgg                                 35

<210> SEQ ID NO 88
<211> LENGTH: 30
<212> TYPE: DNA
<213> ORGANISM: Artificial
<220> FEATURE:
<223> OTHER INFORMATION: An artificially synthesized 3' primer sequence
      for VL

<400> SEQUENCE: 88
cccaagctta ctggatggtg ggaagatgga                                       30
```

ANTI-CDH3 ANTIBODIES AND USES THEREOF

PRIORITY

This application is a U.S. National Phase of PCT/JP2009/007333, filed Dec. 28, 2009, the contents of which is hereby incorporated herein by reference in its entirety for all purposes.

REFERENCE TO SEQUENCE LISTING

This application includes a Sequence Listing as a text file named "87331-028500US-84454_SEQLIST.txt" created Jun. 24, 2012, and containing 47,779 bytes. The material contained in this text file is incorporated by reference in its entirety for all purposes.

TECHNICAL FIELD

The present invention relates to anti-CDH3 antibodies, methods for treating or preventing, or diagnosing a disease associated with CDH3 using the antibodies, and pharmaceutical compositions or diagnosing kits comprising the antibodies.

BACKGROUND ART

Cadherins are cell-cell adhesion glycoproteins that form calcium-dependent inter-cellular junctions and play an essential role in morphogenesis and in the development and maintenance of adult tissues and organs (NPL 1). During embryogenesis, the cell expression of specific cadherins results in homophilic interactions that are critical in the process of cell sorting and tissue stratification (NPL 2-4). Alterations in these cellular attachments play an important role in cell destabilization and may modify the carefully regulated differentiation process of the epithelial structures (NPL 5-6). For this reason, the functional loss or overexpression of cadherins and the molecular mechanisms underlying the control of the genes codifying these proteins have been implicated in carcinogenesis (NPL 7).

The cadherin family is subdivided into various subfamilies, including the classical E-, P-, and N-cadherins, each demonstrating a specific tissue distribution (NPL 8). Although E-cadherin is expressed in all epithelial tissues, the expression of P-cadherin (CDH3) is only restricted to the basal or lower layers of stratified epithelia, including prostate and skin, and also to the breast myoepithelial cells (NPL 9-10).

A large body of evidence now also reveals that aberrant P-cadherin expression is associated with cell proliferation and with tumors of the colon, breast, lung, thyroid, and cervix (NPL 11-12). Human P-cadherin was reported to be the antigen recognized by the NCC-CAD-299 monoclonal antibody raised against a vulvar epidermoid carcinoma (NPL 10). Modulation of P-cadherin mediated adhesion and intracellular signaling is expected to result in decreased proliferation and survival of tumor cells in vivo. Accordingly, in view of the pivotal role that P-cadherin appears to possess in cell proliferation and solid tumor progression, it is desirable to generate antibodies to P-cadherin that can provide a therapeutic benefit to patients with a variety of cancers.

Monoclonal antibodies against cancer-specific molecules have been proved to be useful in cancer treatment (NPL 13). In addition to successful examples of clinical application of the humanized or chimeric antibodies such as trastuzumab (NPL 14), rituximab (NPL 15) and bevacizumab (NPL 16) for breast cancer, malignant lymphoma and colon cancer, a number of monoclonal antibodies against other molecular targets are in development and being evaluated their anti-tumor activities. These monoclonal antibodies are expected to provide a hope to patients having tumors that have no effective treatment. One of the other important issues for these monoclonal antibodies is achievement of selective therapeutic effects to cancer cells without severe toxicity due to their specific reaction to cells expressing target molecules (NPL 17-19, PTL 1-4).

CITATION LIST

Patent Literature

PTL 1: WO2002/097395
PTL 2: WO2004/110345
PTL 3: WO2006/114704
PTL 4: WO2007/102525

Non Patent Literature

NPL 1: Conacci-Sorrell M, et al., J Clin Invest, 109:987-91, (2002
NPL 2: Nose A, et al., Cell, 54:993-1001, (1988)
NPL 3: Steinberg M S, et al., Proc Natl Acad Sci USA, 91:206-9, (1994)
NPL 4: Takeichi M. Science, 251:1451-5, (1991)
NPL 5: Daniel C W, et al., Dev Biol, 169:511-9, (1995)
NPL 6: Nose A and Takeichi M. J Cell Biol, 103:2649-58, (1986)
NPL 7: Behrens J. Cancer Metastasis Rev, 18:15-30 (1999)
NPL 8: Takeichi M. Development, 102:639-55 (1988)
NPL 9: Takeichi M. J Cell Biol 103:2649-58, (1986)
NPL 10: Shimoyama Y, et al., Cancer Res, 49:2128-33 (1989)
NPL 11: Gamallo, Modern Pathology, 14:650-654, (2001)
NPL 12: Stefansson, et al., J. Clin. Oncol. 22(7):1242-1252 (2004)
NPL 13: Harris, M. Lancet Oncol, 5: 292-302 (2004)
NPL 14: Baselga, J. Oncology, 61: SuuplSuupl 2 14-21 (2004)
NPL 15: Maloney, D. G., et al. Blood, 90: 2188-2195 (1997)
NPL 16: Ferrara, N., et al. Nat Rev Drug Discov, 3: 391-400 (2004)
NPL 17: Crist, W. M., et al. J Clin Oncol, 19: 3091-3102 (2001)
NPL 18: Wunder, J. S., et al. J Bone Joint Surg Am, 80: 1020-1033 (1998)
NPL 19: Ferguson, W. S. and Goorin, A. M. Cancer Invest, 19: 292-315 (2001)

SUMMARY OF INVENTION

The present invention provides monoclonal antibodies against CDH3, which specifically recognize a CDH3 polypeptide such as a polypeptide having the amino acid sequence as shown in SEQ ID NO: 2 or a fragment thereof. The present invention provides an evidence that 90Y-labeled anti-CDH3 monoclonal antibodies have significant antitumor effect in xenograft mice bearing a cancer cell line.

Specifically, the present invention relates to the following:
[1] An antibody or a fragment thereof, wherein the antibody comprises an H (heavy) chain V (variable) region and an L (light) chain V region, wherein the H chain V region and the L chain V region selected from the group consisting of:
(a) an H chain V region comprising complementarity determining regions (CDRs) included in an H chain V region having the amino acid sequence shown in SEQ ID NO: 4 or CDRs functionally equivalent thereto, and an L chain V region comprising CDRs included in an L chain V region having the amino acid sequence shown in SEQ ID NO 12 or CDRs functionally equivalent thereto;

(b) an H chain V region comprising CDRs included in an H chain V region having the amino acid sequence shown in SEQ ID NO: 20 or CDRs functionally equivalent thereto, and an L chain V region comprising CDRs included in an L chain V region having the amino acid sequence shown in SEQ ID NO: 28 or CDRs functionally equivalent thereto;

(c) an H chain V region comprising CDRs included in an H chain V region having the amino acid sequence shown in SEQ ID NO: 36 or CDRs functionally equivalent thereto, and an L chain V region comprising CDRs included in an L chain V region having the amino acid sequence shown in SEQ ID NO 44 or CDRs functionally equivalent thereto; and (d) an H chain V region comprising CDRs included in an H chain V region having the amino acid sequence shown in SEQ ID NOs: 68, 72, 76 or 80, or CDRs functionally equivalent thereto, and an L chain V region comprising CDRs included in an L chain V region having the amino acid sequence shown in SEQ ID NO: 60 or CDRs functionally equivalent thereto, and wherein the antibody is capable of binding to a CDH3 polypeptide or a partial peptide thereof.

In typical embodiments, the antibody is selected from the group consisting of a mouse antibody, a chimeric antibody, a humanized antibody, a human antibody, an antibody fragment, and single-chain antibody.

[2] The antibody or fragment thereof of the present invention can be conjugated with a cytotoxic, a therapeutic agent, a radioisotope label or a fluorescent label. In typical embodiments, the antibody is labeled with a radioisotope label. In more typical embodiments, the radioisotope label is selected from the group consisting of 90yttrium ($^{90}Y$), 125iodine ($^{125}I$) and 111indium ($^{111}In$).

[3] A method for treating or preventing a disease associated with CDH3, or inhibiting CDH3-expressing cells grow, in a subject, the method comprising administering to the subject an effective amount of the antibody or fragment thereof of the present invention.

[4] A method for diagnosis or prognosis of a disease that is associated with CDH3 or of a predisposition to develop the disease in a subject, comprising (a) contacting a sample or a specimen from the subject with the antibody or fragment of the invention;

(b) detecting a CDH3 polypeptide in the sample or specimen; and (c) determining whether or not the subject suffers from or is at risk of developing the disease based on the relative abundance of the CDH3 polypeptide compared to a control.

[5] A pharmaceutical composition, for treating or preventing a disease associated with CDH3, or inhibiting CDH3-expressing cells growth, the composition comprising an effective amount of the antibody or fragment thereof of the present invention, and a pharmaceutically acceptable carrier or excipient.

[6] A kit for diagnosis or prognosis of a disease associated with CDH3, the kit comprising the antibody or fragment of the present invention.

DESCRIPTION OF EMBODIMENTS

Figure 1:
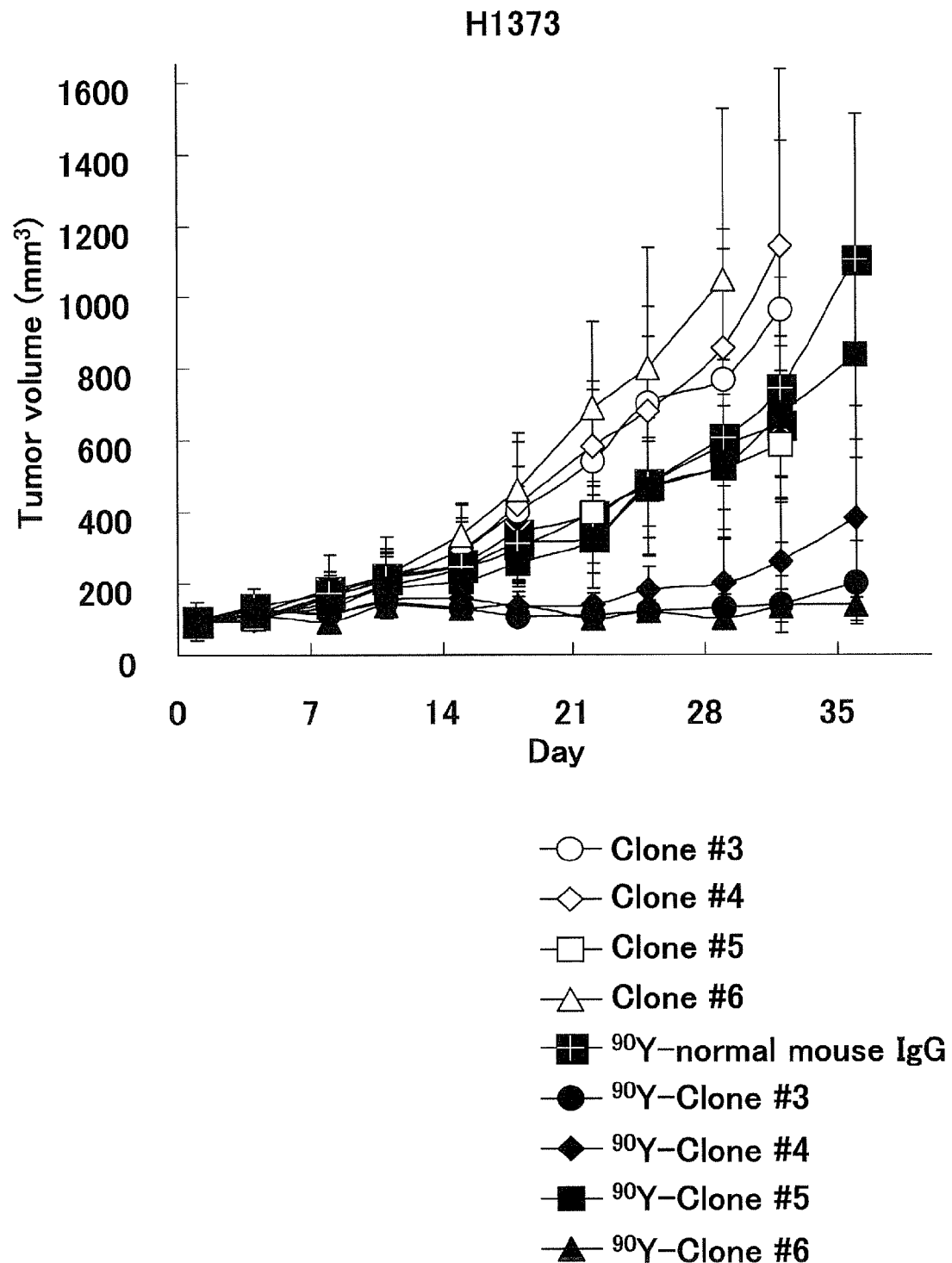
FIG. 1 shows the effect of 90Y-labeled anti-CDH3 antibodies (clone #3, #4, #5 and #6) on tumor growth. 90Y-labeled anti-CDH3 antibodies, in particular clone #3, #4 and #6, effectively suppressed the growth of H1373 cells grafted in nude mice, while no suppression of tumor growth was demonstrated by administration of non-labeled anti-CDH3 antibodies.

The present invention relates to anti-CDH3 antibodies, compositions comprising them and their use in treating or preventing a disease associated with CDH3 such as cancer. In a typical embodiment, the antibody is labeled with a radioisotope label.

cDNA microarrays for gene expression analysis of pancreatic cancer cells and normal cells collected from pancreatic cancer patients has been reported (Nakamura et al., (2004) Oncogene; 23: 2385-400). A number of genes with specifically enhanced expression in pancreatic cancer cells were subsequently identified. Placental cadherin (P-cadherin; CDH3), which is a cytoplasmic membrane protein, was one of these genes and represented low levels of expression in major organs. Such features are suitable for a target gene for cancer therapy because the danger of side effects will be avoided. In addition, a similar over-expression of CDH3 was confirmed in other cancer cell lines, such as the lung, colorectal, prostate, breast, gastric and liver-cancer cell lines (WO/2007/102525).

DEFINITION

The terms "antibody" as used herein is intended to include immunoglobulins and fragments thereof which are specifically reactive to the designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

"Antibody fragments" is a portion of an intact antibody, generally comprises one or more antigen binding or variable regions of the intact antibody. Accordingly, in the present invention, antibody fragments may comprise one or more antigen binding portions of the intact antibody. The term "antigen-binding portion" of an antibody, as used herein, refers to one or more immunological active fragments of an antibody that retain the ability to specifically bind to an antigen (e.g., CDH3). It has been shown that the antigen-binding function of an antibody can be performed by fragments of a full-length antibody. Examples of antibody fragments include Fab, Fab', F(ab')2, and Fv fragments; linear antibodies; and single chain antibody molecules. Regardless of structure, an antibody fragment binds with the same antigen that is recognized by the intact antibody. The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

The term "functionally equivalent" to the CDRs as used herein, refers to CDRs that give an antibody having them substantially equal antigen-binding activity and antigen specificity to the antibody having original CDRs. Examples of functionally equivalent to the CDRs include those wherein one or more amino acid residues are substituted, deleted, inserted and/or added to the original CDRs. So long as the antigen binding activity and antigen specificity are maintained, the number or percentage of amino acid mutations are not particularly limited. However, it is generally preferred to alter 20% or less of the amino acid sequence of original CDRs included in a variable region. More preferably, percentage of mutations is 15% or less, 10% or less, 5% or less. In preferred embodiment, the number of amino acid mutations is 10 or less, 5 or less, 4 or less, 3 or less, 2 or less, 1 or less. One skilled in the art will understand acceptable mutations which retain the properties of the original CDRs.

Production of Antibodies

The present invention uses monoclonal anti-CDH3 antibodies. These antibodies will be provided by methods well known in the art.

Exemplary techniques for the production of the antibodies used in accordance with the present invention are described below.

(i) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256: 495 (1975), or may be made by recombinant DNA methods (U.S. Pat. No. 4,816,567).

In the hybridoma method, a mouse or other appropriate host animal, such as a hamster, is immunized with a CDH3 polypeptide to elicit lymphocytes that produce or are capable of producing antibodies that will specifically bind to CDH3 polypeptides. Alternatively, lymphocytes may be immunized with a CDH3 polypeptide in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas can typically include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Preferred myeloma cell lines include murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Manassas, Va., USA.

Human myeloma and mouse-human heteromyeloma cell lines also have been described for the production of human monoclonal antibodies (Kozbor, J. Immunol., 133: 300 1 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the 30 Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPML-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5: 256-262 (1993) and Pluckthun, Immunol. Revs., 130: 151-188 (1992).

Another method of generating specific antibodies, or antibody fragments, reactive against a CDH3 is to screen expression libraries encoding immunoglobulin genes, or portions thereof, expressed in bacteria with a CDH3 protein or peptide. For example, complete Fab fragments, VH regions and Fv regions can be expressed in bacteria using phage expression libraries. See for example, Ward et al., Nature 341: 544-546 (1989); Huse et al., Science 246: 1275-1281 (1989); and McCafferty et al., Nature 348: 552-554 (1990). Screening such libraries with, for example, a CDH3 peptide, can identify immunoglobulin fragments reactive with CDH3. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., Nature, 348: 552-554 (1990). Clackson et al., Nature, 352: 624-628 (1991) and Marks et al., J MoL Biol., 222: 581-597 (1991) describe the isolation of murine and human antibodies, respectively, using phage libraries. Subsequent publications describe the production of high affinity (nM range) human antibodies by chain shuffling (Marks et al., BioTechnology, 10: 779-783 (1992)), as well as combinatorial infection and in vivo recombination as a strategy for constructing very large phage libraries (Waterhouse et al., Nuc. Acids. Res., 21: 2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. ScL USA, 81: 6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen combining site of an antibody to create a chimeric bivalent antibody comprising one antigen-combining site having specificity for an antigen and another antigen-combining site having specificity for a different antigen.

The present invention provides antibodies suitable for treating and/or preventing a disease, and/or inhibiting CDH3-expressing cells growth. The present invention also provides antibodies suitable for diagnosing CDH3 associated disease. In the present invention, murine monoclonal antibodies clone #3, #4 and #5 are successfully established and these antibodies, in particular clone #3, were demonstrated to effectively suppress CDH3-expressing cells (e.g., cancer cells) growth. Further, these clones have no glycosylation sites within their variable regions. This property is an advantage for developing of therapeutic drugs since it may support uniformity of the antibody.

Also, in the present invention, variants, which have no glycosylation sites, of clone #6 are successfully established. Clone #6 have been demonstrated as a antibodies which has capability of inhibit various CDH3-expressing cells growth, however, it has a glycosylation site within CDR2 of the H chain V region. The variants of the present invention are changed an asparagine residue of glycosylation site to a serine, threonine, alanine or glutamine residue.

The amino acid sequences of H chain V region of mouse monoclonal antibodies clone #3, clone #4 and #5 are shown in SEQ ID NOs: 4, 20, 36, respectively. The amino acid sequences of L chain V region of mouse monoclonal antibodies clone #3, clone #4 and #5 are shown in SEQ ID NOs: 12, 28, 44, respectively. Further, the amino acid sequences of H chain V region of variants of clone #6 are shown in SEQ ID NOs: 68, 72, 76 and 80, respectively. The amino acid sequences of L chain V region of variants of clone #6 are shown in SEQ ID NO: 60.

CDRs included in an H chain V region and an L chain V region can be determined according to methods well-known in the art. For example, the methods described by Kabat et al (Kabat E. A. et al. (1991) Sequence of Proteins of Immunological Interest. 5th Edition) or Chothia et al (Chothia et al. J. Mol. Biol. (1987) 196; 901-917) are generally used for CDRs determination.

Therefore, the present invention provides antibodies or fragments thereof, comprising an H chain V region and an L chain V region, wherein the H chain V region and the L chain V region selected from the group consisting of:

(a) an H chain V region comprising CDRs included in an H chain V region having the amino acid sequence shown in SEQ ID NO: 4 or CDRs functionally equivalent thereto, and an L chain V region comprising CDRs included in an L chain V region having the amino acid sequence shown in SEQ ID NO: 12 or CDRs functionally equivalent thereto;

(b) an H chain V region comprising CDRs included in an H chain V region having the amino acid sequence shown in SEQ ID NO: 20 or CDRs functionally equivalent thereto, and an L chain V region comprising CDRs included in an L chain V region having the amino acid sequence shown in SEQ ID NO: 28 or CDRs functionally equivalent thereto;

(c) an H chain V region comprising CDRs included in an H chain V region having the amino acid sequence shown in SEQ ID NO: 36 or CDRs functionally equivalent thereto, and an L chain V region comprising CDRs included in an L chain V region having the amino acid sequence shown in SEQ ID NO: 44 or CDRs functionally equivalent thereto; and (d) an H chain V region comprising CDRs included in an H chain V region having the amino acid sequence shown in SEQ ID NOs: 68, 72, 76 or 80, or CDRs functionally equivalent thereto, and an L chain V region comprising CDRs included in an L chain V region having the amino acid sequence shown in SEQ ID NO 60 or CDRs functionally equivalent thereto, and wherein the antibody is capable of binding to a CDH3 polypeptide or a partial peptide thereof.

In preferred embodiments, CDRs may be determined by the Kabat definition (Kabat E. A. et al. (1991) Sequence of Proteins of Immunological Interest. 5th Edition). The CDRs of each clone determined by the Kabat definition are described below.

```
The amino acid sequences of CDRs of clone #3 are
                                              (SEQ ID NO: 6)
CDR1: SFWIH, (SEQ ID NO: 8)
CDR2: NIDPSDSETHYNQYFKD
and (SEQ ID NO: 10)
CDR3: GGTGFSS
in the H chain V region, and (SEQ ID NO: 14)
CDR1: KASQDIDSYLS, (SEQ ID NO: 16)
CDR2: RANRLVD,
and (SEQ ID NO: 18)
CDR3: LQYDEFPRT
in the L chain V region.

The amino acid sequences of CDRs of clone #4 are
                                              (SEQ ID NO: 21)
CDR1: SYWMH, (SEQ ID NO: 24)
CDR2: NIDPSDSETHYNQNFND
and (SEQ ID NO: 26)
CDR3: GGTGFAY
in the H chain V region, and (SEQ ID NO: 30)
CDR1: KASQDINNYLG, (SEQ ID NO: 32)
CDR2: RTDRLIE,
and (SEQ ID NO: 34)
CDR3: LQYDEFPRM
in the L chain V region.
```

-continued

The amino acid sequences of CDRs of clone #5 are

CDR1: SYWMH, (SEQ ID NO: 38)

CDR2: NIDPSDSETHYNQKFNDRA (SEQ ID NO: 40)
and

CDR3: GGTGFAY (SEQ ID NO: 42)
in the H chain V region, and

CDR1: KASQDINNYLG, (SEQ ID NO: 46)

CDR2: RTDRLIE, (SEQ ID NO: 48)
and

CDR3: LQYDEFPRM (SEQ ID NO: 50)
in the L chain V region.

The amino acid sequences of CDRs of variants of clone #6 are

CDR1: SYWIH, (SEQ ID NO: 54)

CDR2: EIDPSDSYTYYNQNFKG, (SEQ ID NO: 70)

EIDPSDTY-TYYNQNFKG, (SEQ ID NO: 74)

EIDPSDAYTYYNQNFKG (SEQ ID NO: 78)
or

EIDPSDQYTYYNQNFKG (SEQ ID NO: 82)
and

CDR3: SGYGNLFVY (SEQ ID NO: 58)
in the H chain V region, and

CDR1: SATSSVTYMY, (SEQ ID NO: 62)

CDR2: RTSNLAS, (SEQ ID NO: 64)
and

CDR3: QHYHIYPRT (SEQ ID NO: 66)
in the L chain V region.

Therefore, the present invention also provides antibodies or fragments thereof, wherein the antibodies comprises an H chain V region and an L chain V region, wherein the H chain V region and the L chain V region selected from the group consisting of:

(a) an H chain V region comprising CDR1 having the amino acid sequence shown in SEQ ID NO: 6, CDR2 having the amino acid sequence shown in SEQ ID NO: 8 and CDR3 having the amino acid sequence shown in SEQ ID NO: 10, and an L chain V region comprising CDR1 having the amino acid sequence shown in SEQ ID NO: 14, CDR2 having the amino acid sequence shown in SEQ ID NO: 16 and CDR3 having the amino acid sequence shown in SEQ ID NO: 18;

(b) an H chain V region comprising CDR1 having the amino acid sequence shown in SEQ ID NO: 22, CDR2 having the amino acid sequence shown in SEQ ID NO: 24 and CDR3 having the amino acid sequence shown in SEQ ID NO: 26, and an L chain V region comprising CDR1 having the amino acid sequence shown in SEQ ID NO: 30, CDR2 having the amino acid sequence shown in SEQ ID NO: 32 and CDR3 having the amino acid sequence shown in SEQ ID NO: 34;

(c) an H chain V region comprising CDR1 having the amino acid sequence shown in SEQ ID NO: 38, CDR2 having the amino acid sequence shown in SEQ ID NO: 40 and CDR3 having the amino acid sequence shown in SEQ ID NO: 42, and an L chain V region comprising CDR1 having the amino acid sequence shown in SEQ ID NO: 46, CDR2 having the amino acid sequence shown in SEQ ID NO: 48 and CDR3 having the amino acid sequence shown in SEQ ID NO: 50; and (d) an H chain V region comprising CDR1 having the amino acid sequence shown in SEQ ID NO: 54, CDR2 having the amino acid sequence shown in SEQ ID NOs: 70, 74, 78 or 82 and CDR3 having the amino acid sequence shown in SEQ ID NO: 58, and an L chain V region comprising CDR1 having the amino acid sequence shown in SEQ ID NO: 62, CDR2 having the amino acid sequence shown in SEQ ID NO: 64 and CDR3 having the amino acid sequence shown in SEQ ID NO: 66.

An example of the H chain V region (VH) in the above-mentioned "H chain V region comprising CDR1 having the amino acid sequence shown in SEQ ID NO: 6, CDR2 having the amino acid sequence shown in SEQ ID NO: 8 and CDR3 having the amino acid sequence shown in SEQ ID NO: 10" is a VH having the amino acid sequence shown in SEQ ID NO: 4. An example of the L chain V region (VL) in the above-mentioned "L chain V region comprising CDR1 having the amino acid sequence shown in SEQ ID NO: 14, CDR2 having the amino acid sequence shown in SEQ ID NO: 16 and CDR3 having the amino acid sequence shown in SEQ ID NO: 8" is a VL having the amino acid sequence shown in SEQ ID NO: 12.

An example of the VH in the above-mentioned "H chain V region comprising CDR1 having the amino acid sequence shown in SEQ ID NO: 22, CDR2 having the amino acid sequence shown in SEQ ID NO: 24 and CDR3 having the amino acid sequence shown in SEQ ID NO: 26" is a VH having the amino acid sequence shown in SEQ ID NO: 20. An example of the VL in the above-mentioned "L chain V region comprising CDR1 having the amino acid sequence shown in SEQ ID NO: 30, CDR2 having the amino acid sequence shown in SEQ ID NO: 32 and CDR3 having the amino acid sequence shown in SEQ ID NO: 34" is a VL having the amino acid sequence shown in SEQ ID NO: 28.

An example of the VH in the above-mentioned "H chain V region comprising CDR1 having the amino acid sequence shown in SEQ ID NO: 38, CDR2 having the amino acid sequence shown in SEQ ID NO: 40 and CDR3 having the amino acid sequence shown in SEQ ID NO: 42" is a VH having the amino acid sequence shown in SEQ ID NO: 36. An example of the VL in the above-mentioned "L chain V region comprising CDR1 having the amino acid sequence shown in SEQ ID NO: 46, CDR2 having the amino acid sequence shown in SEQ ID NO: 48 and CDR3 having the amino acid sequence shown in SEQ ID NO: 50" is a VL having the amino acid sequence shown in SEQ ID NO: 44.

An example of the VH in the above-mentioned "H chain V region comprising CDR1 having the amino acid sequence shown in SEQ ID NO: 54, CDR2 having the amino acid sequence shown in SEQ ID NOs: 70, 74, 78 or 82 and CDR3 having the amino acid sequence shown in SEQ ID NO: 58" is a VH having the amino acid sequence shown in SEQ ID NO: 68, 72, 76 or 80. An example of the VL in the above-mentioned "L chain V region comprising CDR1 having the amino acid sequence shown in SEQ ID NO: 62, CDR2 having the amino acid sequence shown in SEQ ID NO: 64 and CDR3 having the amino acid sequence shown in SEQ ID NO: 66" is a VL having the amino acid sequence shown in SEQ ID NO: 60.

Therefore, in an embodiment, the present invention provides the antibodies or fragments thereof, wherein the antibody comprises an H chain V region having the amino acid sequence selected from the group consisting of SEQ ID NOs: 4, 20, 36, 68, 72, 76 and 80 and/or an L chain V region having the amino acid sequence selected from the group consisting of SEQ ID NOs: 12, 28, 44 and 60.

In preferred embodiments, the antibodies of the present invention comprises:

(a) an H chain V region having the amino acid sequence shown in SEQ ID NO: 4 and an L chain V region having the amino acid sequence shown in SEQ ID NO: 12;

(b) an H chain V region having the amino acid sequence shown in SEQ ID NO: 20 and an L chain V region having the amino acid sequence shown in SEQ ID NO: 28;

(c) an H chain V region having the amino acid sequence shown in SEQ ID NO: 36 and an L chain V region having the amino acid sequence shown in SEQ ID NO: 44; or (d) an H chain V region having the amino acid sequence shown in SEQ ID NOs: 68, 72, 76 or 80 and an L chain V region having the amino acid sequence shown in SEQ ID NO: 60.

The antibodies of the present invention can be prepared by conventional methods. For example, the antibodies may be prepared by integrating a polypeptide encoding the antibody polypeptide into a suitable vector, introducing the vector into a host, and producing the antibody from the host according to a conventional genetic recombination technique (see, for example, Vandamme, A. M. et al., Eur. J. Biochem. (1990) 192, 767-75).

The nucleic acid sequences of the polynucleotides encoding the V regions of the antibodies of the present invention can be deduced from the amino acid sequences of the V regions of the antibodies of the present invention. For example, the nucleic acid sequences shown in SEQ ID NOs: 3 and 11 may be used as the nucleic acid sequences encoding the VH and VL of clone #3, respectively. For example, the nucleic acid sequences shown in SEQ ID NOs: 19 and 27 may be used as the nucleic acid sequences encoding the VH and VL of clone #4, respectively. For example, the nucleic acid sequences shown in SEQ ID NOs: 35 and 43 may be used as the nucleic acid sequences encoding the VH and VL of clone #5, respectively. For example, the nucleic acid sequences shown in SEQ ID NOs: 67, 71, 75 or 79, and 59 may be used as the nucleic acid sequences encoding the VH and VL of variants of clone #6, respectively. The polynucleotides encoding the V region of the antibodies of the present invention can be synthesized based on the sequence information by conventional methods such as the solid phase techniques (Beaucage S L & Iyer R P, Tetrahedron (1992) 48, 2223-311; Matthes et al., EMBO J (1984) 3, 801-5) and oligonucleotide synthesis techniques (Jones et al. Nature (1986) 321, 522-5).

The polynucleotide encoding the antibody V region are integrated into an expression vector containing polynucleotide encoding the antibody constant (C) region.

For the production of the antibody used in the present invention, the polypeptide encoding the antibody (antibody gene) is integrated into an expression vector so that the antibody gene can be expressed under the control of expression control elements (e.g., enhancer, promoter). A host cell is transformed with the expression vector to express the antibody.

In the expression of the antibody gene, the polynucleotide encoding H chain and polynucleotide encoding L chain of the antibody may be integrated into separate expression vectors, and then a host cell is co-transformed with the resultant recombinant expression vectors. Alternatively, both polynucleotide encoding H chain and polynucleotide encoding L chain of the antibody may be integrated together into a single expression vector, and then a host cell is transformed with the resultant recombinant expression vector (for example, WO 94/11523).

The antibody gene can be expressed by known methods. For the expression in a mammalian cell, a conventional useful promoter, the antibody gene to be expressed and a poly(A) signal (located downstream to the 3' end of the antibody gene) may be operably linked. For example, as the useful promoter/enhancer system, a human cytomegalovirus immediate early promoter/enhancer system may be used.

Other promoter/enhancer systems, for example, those derived from viruses (e.g., retrovirus, polyoma virus, adenovirus and simian virus 40 (SV40)) and those derived from mammalian cells (e.g., human elongation factor 1 alpha (HEF1 alpha)), may also be used for the expression of the antibody in the present invention.

When SV40 promoter/enhancer system is used, the gene expression may be performed readily by the method of Mulligan et al. (Nature (1979) 277, 108-14.). When HEF1 alpha promoter/enhancer system is used, the gene expression may be performed readily by the method of Mizushima et al. (Nucleic Acids Res. (1990) 18, 5322.).

For the expression in *E. coli*, a conventional useful promoter, a signal sequence for secreting the antibody of interest and the antibody gene may be operably linked. As the promoter, lacZ promoter or araB promoter may be used. When lacZ promoter is used, the gene expression may be performed by the method of Ward et al. (Nature (1098) 341, 544-6.; FASBE J. (1992) 6, 2422-7.), while when araB promoter is used, the gene expression may be performed by the method of Better et al. (Science (1988) 240, 1041-3.).

With respect to the signal sequence for secretion of the antibody, when the antibody of interest is intended to be secreted in a periplasmic space of the *E. coli*, pelB signal sequence (Lei, S. P. et al, J. Bacteriol. (1987) 169, 4379-83.) may be used. The antibody secreted into the periplasmic space is isolated and then refolded so that the antibody takes an appropriate configuration.

The replication origin derived from viruses {e.g., SV40, polyoma virus, adenovirus, bovine papilloma virus (BPV)) or the like may be used. In order to increase the gene copy number in the host cell system, the expression vector may further contain a selective marker gene, such as an aminoglycoside phosphotransferase (APH) gene, a thymidine kinase (TK) gene, an *E. coli* xanthine-guanine phosphoribosyltransferase (Ecogpt) gene and a dihydrofolate reductase (dhfr) gene. For the production of the antibody used in the present invention, any expression system including eukaryotic and prokaryotic cell systems may be used. The eukaryotic cell includes established cell lines of animals (e.g., mammals, insects, molds and fungi, yeast). The prokaryotic cell includes bacterial cells such as *E. coli* cells. It is preferable that the antibody used in the present invention be expressed in a mammalian cell, such as a CHO, COS, myeloma, BHK, Vero and HeLa cell.

Next, the transformed host cell is cultured in vitro or in vivo to produce the antibody of interest. The cultivation of the host cell may be performed by any known method. The culture medium that can be used herein may be DMEM, MEM, RPMI 1640 or IMDM medium. The culture medium may contain a serum supplement, such as fetal calf serum (FCS).

In the production of the recombinant antibody, besides the above-mentioned host cells, a transgenic animal may also be used as a host. For example, the antibody gene is inserted into a predetermined site of a gene encoding a protein inherently produced in the milk of an animal (e.g., beta-casein) to prepare a fusion gene. A DNA fragment containing the antibody gene-introduced fusion gene is injected into an embryo of a non-human animal, and the embryo is then introduced into a female animal. The female animal having the embryo therein bears a transgenic non-human animal. The antibody of interest is secreted in the milk from the transgenic non-human animal or a progeny thereof. For the purpose of increasing the amount of the antibody-containing milk, an appropriate hormone may be administered to the transgenic animal (Ebert, K. M. et al, Bio/Technology (1994) 12, 699-702.).

The antibody expressed and produced as described above may be isolated from the cells or the host animal body and purified. The isolation and purification of the antibody used in the present invention may be performed on an affinity column. Other methods conventionally used for the isolation and purification of an antibody may be also be used; thus the method is not particularly limited. For example, various chromatographies, filtration, ultrafiltration, salting out and dialysis may be used singly or in combination to isolate and purify the antibody of interest (Antibodies A Laboratory Manual. Ed. Harlow, David Lane, Cold Spring Harbor Laboratory, 1988).

(ii) Chimeric Antibody and Humanized Antibody

In the present invention, an artificially modified recombinant antibody may be used, including a chimeric antibody and a humanized antibody. These modified antibodies can be prepared by any known method. For example, techniques developed for the production of "chimeric antibodies" (Morrison et al., Proc. Natl. Acad. ScL, (1984) 81: 6851-5.; Neuberger et al., Nature (1984), 312: 604-8.; Takeda et al., Nature (1985) 314: 452-4.) can be used.

A chimeric antibody is a molecule in which different portions are derived from different animal species, such as those having a variable region derived from a murine monoclonal antibody and a human immunoglobulin constant region, e.g., "humanized antibodies".

A chimeric antibody according to the present invention can be prepared by ligating the DNA encoding the antibody V region to DNA encoding a human antibody C region, integrating the ligation product into an expression vector, and introducing the resultant recombinant expression vector into a host to produce the chimeric antibody.

A humanized antibody is also referred to as "reshaped human antibody", in which the CDRs of an antibody of a non-human mammal (e.g., a mouse) are grafted to those of a human antibody. The general genetic recombination procedure for producing such humanized antibody is also known (for example, EP 125023; WO 96/02576.).

Specifically, a nucleic acid sequence in which mouse antibody CDRs are ligated through framework regions (FRs) is designed, and synthesized by a PCR method using several oligonucleotides as primers which were designed to have regions overlapping to the terminal regions of the CDRs and the FRs. The resultant DNA is ligated to DNA encoding the human antibody C-region, and the ligation product is integrated into an expression vector. The resultant recombinant expression vector is introduced into a host, thereby producing the humanized antibody (for example, WO 96/02576).

The FRs ligated through the CDRs are selected so that the CDRs can form a functional antigen binding site. If necessary, an amino acid(s) in the FRs of the antibody V region may be replaced so that the CDRs of the reshaped human antibody can form an appropriate antigen binding site (Sato, K. et al., Cancer Res. (1993) 53, 851-6.).

The chimeric antibody is composed of V regions derived from a non-human mammal antibody and C-regions derived from a human antibody. The humanized antibody is composed of CDRs derived from a non-human mammal antibody and FRs and C regions derived from a human antibody. The humanized antibody may be useful for clinical use, because the antigenicity of the antibody against a human body is reduced.

A specific example of a chimeric antibody or a humanized antibody used in the present invention is an antibody in which the V regions are derived from the mouse monoclonal antibody clone #3, #4, #5 or variants of clone #6, or an antibody in which the CDRs are derived from the mouse monoclonal antibody clone #3, #4, #5 or variants of clone #6. The method for producing such chimeric antibodies and humanized antibodies are described below.

For example, first, the genes encoding the V regions or CDRs of the antibodies of clone #3, #4, #5 or variants of clone #6 are prepared from the RNAs of antibody-producing cells by polymerase chain reaction (PCR) or such (see, for example, Larrick et al., "Methods: a Companion to Methods in Enzymology", Vol. 2: 106, 1991; Courtenay-Luck, "Genetic Manipulation of Monoclonal Antibodies" in Monoclonal Antibodies: Production, Engineering and Clinical Application; Ritter et al. (eds.), page 166, Cambridge University Press, 1995, and Ward et al., "Genetic Manipulation and Expression of Antibodies" in Monoclonal Antibodies: Principles and Applications; and Birch et al. (eds.), page 137, Wiley-Liss, Inc., 1995). The polynucleotides encoding the V regions or CDRs of the antibodies may be synthesized oligonucleotide synthesis techniques (e.g., Jones et al. Nature (1986) 321, 522-5). Then, the amplified or synthesized products are subjected to agarose gel electrophoresis according to conventional procedures, and DNA fragments of interest are excised, recovered, purified and ligated to a vector DNA.

The obtained DNA and vector DNA can be ligated using a known ligation kit to construct a recombinant vector. A vector DNA may be prepared in a known method: J. Sambrook, et al., "Molecular Cloning", Cold Spring Harbor Laboratory Press, 1989. The vector DNA is digested with restriction enzyme(s), and the nucleotide sequence of a desired DNA can be determined by a known method or using an automated sequencer.

Once DNA fragments encoding for L and H chain V regions of mouse monoclonal antibody (hereinafter L or H chain of an antibody may sometimes be referred to as "mouse L or H chain" for mouse antibodies and "human L or H chain" for human antibodies) are cloned, the DNAs encoding mouse V regions and DNAs encoding human antibody C regions are ligated and expressed to yield chimeric antibodies.

A standard method for preparing chimeric antibodies involves ligating a mouse signal sequence and V region sequence present in a cloned cDNA to a sequence encoding for a human antibody C region already present in an expression vector of a mammalian cell. Alternatively, a mouse signal sequence and V region sequence present in a cloned cDNA are ligated to a sequence coding for a human antibody C region followed by ligation to a mammalian cell expression vector.

The polypeptide comprising human antibody C region can be any of H or L chain C regions of human antibodies, including, for example, C gamma 1, C gamma 2, C gamma 3 or C gamma 4 for human H chains or C lambda or C kappa for L chains. To prepare a chimeric antibody, two expression vectors are first constructed; that is, an expression vector containing DNAs encoding mouse L chain V region and human L chain C region under the control of an expression control element such as an enhancer/promoter system, and an expression vector containing DNAs encoding mouse H chain V region and human H chain C region under the control of an expression control element such as an enhancer/promoter system, are constructed. Then, host cells such as mammalian cells (for example, COS cell) are cotransformed with these expression vectors and the transformed cells are cultivated in vitro or in vivo to produce a chimeric antibody (see, for example, WO91/16928).

Alternatively, the mouse signal sequence present in the cloned cDNA and DNAs encoding mouse L chain V region and human L chain C region as well as the mouse signal sequence and DNAs coding for mouse H chain V region and human H chain C region are introduced into a single expression vector (see, for example, WO94/11523) and said vector is used to transform a host cell; then, the transformed host is cultured in vivo or in vitro to produce a desired chimeric antibody. The vector for the expression of H chain of a chimeric antibody can be obtained by introducing cDNA comprising a nucleotide sequence encoding mouse H chain V region (hereinafter referred to also as "cDNA for H chain V region") into a suitable expression vector containing the genomic DNA comprising a nucleic acid sequence encoding H chain C region of human antibody (hereinafter referred to also as "genomic DNA for H chain C region") or cDNA encoding the region (hereinafter referred to also as "cDNA for H chain C region"). The H chain C region includes, for example, C gamma 1, C gamma 2, C gamma 3 or C gamma 4 regions.

The expression vectors having the genomic DNA coding for H chain C region, in particular, those encoding C gamma 1 region, include, for example, HEF-PMh-g gamma 1 (WO92/19759) and DHER-INCREMENT E-RVh-PM1-f (WO92/19759). Alternatively, human C region library can be prepared using cDNA from human PBMC (peripheral blood mononuclear cells) as described previously (Liu, A. Y. et al., Proc. Natl. Acad. Sci. USA, Vol. 84, 3439-43, 1987; Reff, M. E. et al., Blood, Vol. 83, No. 2, 435-45, 1994). When cDNA encoding mouse H chain V region is inserted into these expression vectors, an appropriate nucleic acid sequence can be introduced into the cDNA through PCR method. For instance, PCR may be effected using a PCR primer which is designed such that the cDNA has a recognition sequence for a suitable restriction enzyme at its 5'-end and Kozak consensus sequence immediately before the initiation codon thereof so as to improve the transcription efficiency, as well as a PCR primer which is designed such that said cDNA has a recognition sequence for a suitable restriction enzyme at its 3'-end and a splice donor site for properly splicing the primary transcription products of the genomic DNA to give a mRNA, to introduce these appropriate nucleic acid sequences into the expression vector.

The constructed cDNA encoding mouse H chain V region may be treated with a suitable restriction enzyme(s), then it is inserted into the expression vector to construct a chimeric H chain expression vector containing the genome DNA encoding H chain C region (C gamma 1 region). Alternatively, the constructed cDNA encoding mouse H chain V region may be treated with a suitable restriction enzyme(s), ligated to cDNA coding for the H chain C region C gamma 1, and inserted into an expression vector such as pQCXIH (Clontech) to construct an expression vector containing the cDNA encoding a chimeric H chain.

The vector for the expression of L chain of a chimeric antibody can be obtained by ligating a cDNA coding for mouse L chain V region and a genomic DNA or cDNA coding for L chain C region of a human antibody and introducing into a suitable expression vector. The L chain C region includes, for example, kappa chain and lambda chain. When an expression vector containing cDNA encoding mouse L chain V region is constructed, appropriate nucleic acid sequences such as a recognition sequence or Kozak consensus sequence can be introduced into said expression vector through PCR method.

The entire nucleic acid sequence of cDNA encoding human L lambda chain C region may be synthesized by a DNA synthesizer and constructed through PCR method. The human L lambda chain C region is known to have at least 4 different isotypes and each isotype can be used to construct an expression vector. The constructed cDNA encoding human L lambda chain C region and the above constructed cDNA encoding mouse L chain V region can be ligated between suitable restriction enzyme sites and inserted into an expression vector such as pQCXIH (Clontech), to construct an expression vector containing cDNA coding for a L lambda chain of a chimeric antibody. The DNA encoding human L kappa chain C region to be ligated to the DNA coding for mouse L chain V region can be constructed from, for example, HEF-PM1 k-gk containing the genomic DNA (see WO92/19759). Alternatively, human C region library can be prepared using cDNA from human PBMC (peripheral blood mononuclear cells) as described previously (Liu, A. Y. et al., Proc. Natl. Acad. Sci. USA, Vol. 84, 3439-43, 1987; Reff, M. E. et al., Blood, Vol. 83, No. 2, 435-45, 1994).

Recognition sequences for suitable restriction enzymes can be introduced, through PCR method, into 5'- and 3'-ends of DNA coding for L kappa chain C region, and the DNA coding for mouse L chain V region as constructed above and the DNA encoding L kappa chain C region can be ligated to each other and inserted into an expression vector such as pQCXIH (Clontech) to construct an expression vector containing cDNA encoding L kappa chain of a chimeric antibody.

Humanization of non-human antibodies can be essentially performed following the method of Winter and co-workers (Jones et al., Nature, 321: 522-525 (1986); Reichmann et al., Nature, 332: 323-327 (1988); Verhoeyen et al., Science, 239: 1534-1536 (1988)), by substituting CDR sequences for the corresponding sequences of a human antibody.

In order to make a humanized antibody in which CDR of a mouse monoclonal antibody is grafted to a human antibody, it is desirable that there exists a high homology between FR of the mouse monoclonal antibody and FR of the human antibody. Accordingly, a comparison is made between V regions of H and L chains of mouse monoclonal antibody clone #3, #4, #5 or variants of clone #6, and the V regions of all the known antibodies whose structures have been elucidated with the use of Protein Data Bank. Further, they are simultaneously compared with the human antibody subgroups (HSG: Human subgroup) classified by Kabat et al. based on the length of antibody FR, the homology of amino acids, and the like (Kabat, E'. A. et al, US Dep, Health and Human Services, US Government Printing Offices, 1991).

The first step for designing DNA encoding a humanized antibody V region is to select a human antibody V region as a basis for the designing. For example, FR of a human antibody V region having a homology of higher than 80% with FR of a mouse antibody V region can be used in the production of a humanized antibody.

In the humanized antibody, the C region and the framework (FR) regions of the V region of the antibody are originated from human and the CDRs of the V region are originated from mouse. A polypeptide comprising the V region of the humanized antibody can be produced in the manner called CDR-grafting by PCR method so long as a DNA fragment of a human antibody would be available as a template. The "CDR-grafting" refers to a method wherein a DNA fragment encoding a mouse-derived CDRs are made and replaced for the CDRs of a human antibody as a template. If a DNA fragment of a human antibody to be used as a template is not available, a nucleic acid sequence registered in a database may be synthesized in a DNA synthesizer and a DNA for a V region of a humanized antibody can be produced by the PCR method. Further, when only an amino acid sequence is registered in the database, the entire nucleic acid sequence may be deduced from the amino acid sequence on the basis of knowledge on the codon usage in antibodies as reported by Kabat, E. A. et al. in US Dep. Health and Human Services, US Government Printing Offices, 1991. This nucleic acid sequence is synthesized in a DNA synthesizer and a DNA of a humanized antibody V region can be prepared by PCR method and introduced into a suitable host followed by expression thereof to produce the desired polypeptide. General procedures of CDR-grafting by PCR method are described below when a DNA fragment of a human antibody as a template is available.

First, mouse derived DNA fragments corresponding to respective CDRs are synthesized. CDRs 1 to 3 are synthesized on the basis of the nucleic acid sequences of the previously cloned mouse H and L chain V regions. For example, when a humanized antibody is produced based on the mouse monoclonal antibody clone #3, CDR sequences of H chain V region can be the amino acid sequences as shown in SEQ ID NOs: 6 (VH CDR1), 8 (VH CDR2) and 10 (VH CDR3); and CDR sequences of L chain V region can be the amino acid sequences as shown in SEQ ID NOs: 14 (VL CDR1), 16 (VL CDR2) and 18 (VL CDR3). When a humanized antibody is produced based on the mouse monoclonal antibody clone #4, CDR sequences of H chain V region can be the amino acid sequences as shown in SEQ ID NOs: 22 (VH CDR1), 24 (VH CDR2) and 26 (VH CDR3); and CDR sequences of L chain V region can be the amino acid sequences as shown in SEQ ID NOs: 30 (VL CDR1), 32 (VL CDR2) and 34 (VL CDR3). When a humanized antibody is produced based on the mouse monoclonal antibody clone #5, CDR sequences of H chain V region can be the amino acid sequences as shown in SEQ ID NOs: 38 (VH CDR1), 40 (VH CDR2) and 42 (VH CDR3); and CDR sequences of L chain V region can be the amino acid sequences as shown in SEQ ID NOs: 46 (VL CDR1), 48 (VL CDR2) and 50 (VL CDR3). When a humanized antibody is produced based on the mouse monoclonal antibody variants of clone #6, CDR sequences of H chain V region can be the amino acid sequences as shown in SEQ ID NOs: 54 (VH CDR1), 70, 74, 78, or 82 (VH CDR2) and 66 (VH CDR3); and CDR sequences of L chain V region can be the amino acid sequences as shown in SEQ ID NOs: 62 (VL CDR1), 64 (VL CDR2) and 66 (VL CDR3).

The DNA for H chain V region of a humanized antibody may be ligated to DNA for any human antibody H chain C region, for example, human H chain C gamma 1 region. As mentioned above, the DNA for H chain V region may be treated with a suitable restriction enzyme and ligated to a DNA encoding a human H chain C region under an expression control element such as an enhancer/promoter system to make an expression vector containing DNAs for a humanized H chain V region and a human H chain C region.

The DNA for L chain V region of a humanized antibody may be ligated to DNA for any human antibody L chain C region, for example, human L chain C lambda region. The DNA for L chain V region may be treated with a suitable restriction enzyme and ligated to a DNA encoding a human L lambda chain C region under an expression control element such as an enhancer/promoter system to make an expression vector containing DNAs encoding a humanized L chain V region and a human L lambda chain C region.

The DNA encoding H chain V region of a humanized antibody and a human H chain C region and the DNA encoding a humanized L chain V region and human L chain C region may also be introduced into a single expression vector such as that disclosed in WO94/11523, said vector may be used to transform a host cell, and the transformed host may be cultivated in vivo or in vitro to produce a desired humanized antibody.

To produce a chimeric or humanized antibody, two expression vectors as above mentioned should be prepared. Thus, with respect to a chimeric antibody, an expression vector comprising a DNA coding for a mouse H chain V region and a human H chain C region under the control of an expression control element such as an enhancer/promoter, and an expression vector comprising a DNA coding for a mouse L chain V region and a human L chain C region under the control of an expression control element are constructed. With respect to a humanized antibody, an expression vector comprising a DNA encoding a humanized H chain V region and a human H chain C region under the control of an expression control element, and an expression vector comprising a DNA encoding a humanized L chain V region and a human L chain C region under the control of an expression control element are constructed.

Then, a host cell such as a mammalian cell (for example, COS cell) may be cotransformed with these expression vectors and the resulting transformed cell may be cultured in vitro or in vivo to produce the chimeric or humanized antibody (see, for example, WO91/16928). Alternatively, a DNA coding for H chain V and C regions and a DNA encoding L chain V and C regions may be ligated to a single vector and transformed into a suitable host cell to produce an antibody. Thus, in the expression of a chimeric antibody, a DNA coding for a mouse leader sequence present in the cloned cDNA, a mouse H chain V region and a human H chain C region as well as a DNA coding for a mouse leader sequence, a mouse L chain V region and a human L chain C region, can be introduced into a single expression vector such as one disclosed in e.g. WO94/11523. In the expression of a humanized antibody, a DNA encoding a humanized H chain V region and a human H chain C region and a DNA coding for a humanized L chain V region and a human L chain C region may be introduced into a single expression vector such as one disclosed in e.g. WO94/11523. Such a vector is used to transform a host cell and the transformed host is cultured in vivo or in vitro to produce a chimeric or humanized antibody of interest.

Any expression system may be used to produce the chimeric or humanized antibodies of the present invention. For example, eukaryotic cells include animal cells such as established mammalian cell lines, fungal cells, and yeast cells; prokaryotic cells include bacterial cells such as *Escherichia coli*. Preferably, the chimeric or humanized antibody of the present invention is expressed in a mammalian cell such as COS or CHO cell.

Any conventional promoters useful for the expression in mammalian cells may be used. For example, human cytomegalovirus (HCMV) immediate early promoter is preferably used. In addition, promoters for gene expression in mammalian cells may include virus promoters, such as those of retrovirus, polyoma virus, adenovirus and simian virus (SV) 40, and mammalian cell derived promoters, such as those of human polypeptide chain elongation factor-1 alpha (HEF-I alpha). For example, SV40 promoter may be readily used according to Mulligan et al. method (Nature, 277, 108-14, 1979); Mizushima, S. et al. method (Nucleic Acids Research, 18, 5322, 1990) may be easily used with HEF-1 alpha promoter.

Replication origin includes those derived from SV40, polyoma virus, adenovirus or bovine papilloma virus (BPV). Further, the expression vector may comprise a gene for phosphotransferase APH(3') II or I (neo), thymidine kinase (TK), E. coli xanthine-guanine phosphoribosyltransferase (Ecogpt) or dihydrofolate reductase (DHFR) as a selective marker for increasing the gene copy number in a host cell system.

The chimeric or humanized antibody of interest which is thus produced by culturing the transformant transformed with a DNA coding for the chimeric or humanized antibody may be isolated from the cell and then purified.

The isolation and purification of the chimeric or humanized antibody of interest may be carried out by using a protein A agarose column, but may also be performed by any methods used in isolation and purification of a protein and thus is not limited. For instance, a chromatography, ultrafiltration, salting out and dialysis may optionally be selected or combined to isolate and purify the chimeric or humanized antibody.

After isolating the chimeric antibody or humanized antibody, the concentration of the resulting purified antibody can be determined by ELISA.

The determination of the antigen-binding activity or other activities including binding activity to a normal cell of the chimeric antibody or humanized antibody may be performed by any known methods (Antibodies A Laboratory Manual, Ed. Harlow, David Lane, Cold Spring Harbor Laboratory, 1988). As the method for the determination of the antigen-binding activity of an antibody, techniques such as ELISA (enzyme-linked immunosorbent assay), EIA (enzyme immunoassay), RIA (radioimmunoassay) or fluorescent assay may be employed. In ELISA, an antibody is immobilized on a plate, and an antigen for the antibody is added to the plate, then a sample containing the desired antibody, such as the culture supernatant of antibody-producing cells or a purified antibody is added. Next, a secondary antibody which recognizes the primary antibody and is tagged with an enzyme such as alkaline phosphatase is added to the plate, and this is preincubated. After washing, an enzyme substrate such as p-nitrophenyl phosphate is added to the plate, and the absorbance is measured to evaluate the antigen-binding ability of the sample of interest. The evaluation of antigen-binding activity may also be performed using BIAcore (Pharmacia).

To retain the antigen-binding activity, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen, is achieved.

(iii) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F (ab') 2 fragments (Carter et al., Bio/Technology 10: 163-167 (1992)). According to another approach, F (ab') 2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(iv) Bispecific Antibodies

Bispecific antibodies are antibodies that have binding specificities for at least two different epitopes. Exemplary, an anti-cancer cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIH (CD 16) so as to focus cellular defense mechanisms to the cancer cell. Bispecific antibodies may also be used to localize cytotoxic agents to the cancer cell. These antibodies possess a cancer cell marker-binding arm and an arm which binds the cytotoxic agent (e.g. saporin, anti-interferon-a, vinca alkaloid, ricin A chain, methotrexate or radioactive isotope hapten). Bispecific antibodies can be prepared as full length antibodies or antibody fragments (e.g. F (ab) 2 bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305: 537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121: 210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chains are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F (ab') 2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 2 17-225 (1992) describe the production of a fully humanized bispecific antibody F (ab') 2 molecule. Each Fab' fragment was separately secreted from E. coli and subjected to directed chemical coupling in vitro to form the bispecific antibody.

Various techniques for making and isolating bispecific antibody fragments directly from recombinant cell culture have also been described. For example, bispecific antibodies have been produced using leucine zippers (Kostelny et al., J Immunol. 148 (5): 1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90: 6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J Immunol., 152: 5368 (1994).

Antibodies with more than two valencies are contemplated. For example, trispecific antibodies can be prepared. Tutt et al. J; Immunol. 147: 60 (1991).

(v) Antibody Conjugates and Other Modifications

The antibodies of the present invention are optionally conjugated to a cytotoxic or therapeutic agent.

For example, a therapeutic agent includes any chemotherapeutic agent which is useful in the treatment of cancer. Examples of chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembiehin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromoinycins, dactinomycin, daunorubicin, detorubicin, 6-diazo-5-oxo-L-norleucine, doxorubicin, epirubicin, esorubicin, idambicin, marcellomycin, mitomycins, mycophenolic acid, nogalamycin, olivomycins, peplomycin, poffiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK@ razoxane; sizofrran; spirogermanium; tenuazonic acid; triaziquone; 2, 2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rh6ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also, therapeutic agents include anti-hormonal agents that act to regulate or inhibit hormone action on tumors such as anti-estrogens including for example tamoxifen, raloxifene, aromatase inhibiting 4 (5)-imidazoles, 4 hydroxytamoxifen, trioxifene, keoxifene, onapristone, and toremifene (Fareston®); and anti-androgens such as flutamide, nilutamide, bicalutamide, leuprolide, and goserelin; and pharmaceutically acceptable salts, acids or derivatives of any of the above.

Conjugates of an antibody and one or more small molecule toxins, such as a calicheamicin, a maytansine (U.S. Pat. No. 5,208,020), a trichothene, and CC 1065 are also contemplated herein. In one preferred embodiment of the invention, the antibodies are conjugated to one or more maytansine molecules (e.g. about 1 to about 10 maytansine molecules per antibodies molecule). Maytansine may, for example, be converted to May SS-Me which may be reduced to May-SH3 and reacted with modified antibodies (Chari et al. Cancer Research 52: 127-131 (1992)) to generate a maytansinoid-antibody conjugate.

Alternatively, the antibody may be conjugated to one or more calicheamicin molecules. The calicheamicin family of antibiotics is capable of producing double stranded DNA breaks at sub-picomolar concentrations. Structural analogues of calicheamicin which may be used include, but are not limited to gamma1I, alpha2I, alpha3I, N-acetyl-gamma1I, PSAG and OI1 (Hinman et al. Cancer Research 53: 3336-3342 (1993) and Lode et al, Cancer Research 58: 2925-2928 (1998)).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates antibody conjugated with a variety of radioactive isotopes. Examples include $^{111}$In, $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu. In the present invention, the antibody of the present invention may be labeled with radio-nuclides just prior to use, or provided as radiolabeled antibody. The skilled practitioner will realize that there are numerous radionuclides and chemocytotoxic agents that can be coupled to tumor-specific antibodies by well-known techniques and delivered to a site to specifically damaging tumor cells and tissue. (See, for example, U.S. Pat. No. 4,542,225 to W. A. Blattler et al., issued Sep. 17, 1985; and Pastan et al., 1986, Cell, 47:641-648). For example, imaging and cytotoxic reagents that are suitable for use include $^{125}$I, $^{123}$I. $^{111}$In (e.g., Sumerdon et al., 1990, Nucl. Med. Biol., 17:247-254), and 99mTc; fluorescent labels such as fluorescein and rhodamine, chemiluminescent labels such as luciferin, and paramagnetic ions for use in magnetic resonance imaging (Lauffer et al., 1991, Magnetic Resonance in Medicine, 22:339-342). Antibodies can be labeled with such reagents using protocols and techniques known and practiced in the art. See, for example, Wenzel and Meares, Radioimmunoimaging and Radioimmunotherapy, Elsevier, New York, 1983; Colcer et al., 1986, Meth. Enzymol., 121:802-816; and Monoclonal Antibodies for Cancer Detection and Therapy, Eds. Baldwin et al., Academic Press, 1985, pp. 303-316, for techniques relating to the radiolabeling of antibodies. Yttrium-90 (90Y) labeled monoclonal antibodies have been described for maximizing the dose delivered to the tumor or cancer cells and/or tissue, while limiting toxicity to normal tissues (e.g., Goodwin and Meares, 1997, Cancer Supplement, 80:2675-2680). Other cytotoxic radionuclides including, but not limited to, Iodine-131 (131I) and Rhenium-186 can also be used for labeling monoclonal antibodies of the present invention. Among the radionuclides, Yttrium-90 (90Y) may be suitable for radioimmunotherapy, since Yttrium-90 (90Y) provides advantages over Iodine-131 (131I) because it delivers higher beta energy (2.3 MeV vs 0.61 MeV) to the tumor and has path length of 5 to 10 mm resulting in the improved ability to kill both targeted and neighboring cells, an advantage particularly in bulky or poorly vascularized tumor. The detectable/detecting label used is selected according to the imaging modality to be used. For example, radioactive labels, such as Indium-111 ($^{111}$In), Technetium-99m ($^{99m}$Tc), or Iodine 131 ($^{131}$I), can be used for planar scans or for single photon emission computed tomography (SPECT). Also, positron-emitting labels such as Fluorine-19 can be used in positron emission tomography (PET). Paramagnetic ions, such as Gadlinium(III) or Manganese(II) can be used in magnetic resonance imaging (MRI). The monoclonal antibodies can also be labeled with radioopaque labels for the visualization of cancer cells after injection, for example, by X-ray, CATscan, or MRI. In particular, for CDH3 relating disease (e.g. cancers), localization of the label within the cancers permits the determination of the spread of the disease. The amount of label that is present and detectable within the cancers expressing CDH3, for example, allows the determination of the presence or absence of cancer or tumor in the subject to be diagnosed.

Conjugates of the antibody and cytotoxic agent may be made using a variety of bifunctional protein coupling agents such as N-succinimidyl-3-(2-pyriylditliol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1 isothiocyanatobenzyl-3-methyldiethylene triaminepentaacetic acid (MX-DTPA) is an exemplary chelating agent for conjugation of radionucleotide to the antibody (See WO94/11026). The linker may be a "cleavable linker" facilitating release of the cytotoxic drug in the cell. For example, an acid-labile linker, peptidase-sensitive linker, dimethyl linker or disulfide-containing linker (Charm et al. Cancer Research 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

The antibodies of the present invention may also be conjugated with a prodrug activating enzyme which converts a prodrug (e.g. a peptidyl chemotherapeutic agent, see WO81/01145) to an active anti-cancer drug (See, for example, WO 88/07378 and U.S. Pat. No. 4,975,278).

The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as 13-galactosidase and neuraminidase useful for converting glycosylated prodrugs into free drugs; 13-lactamase useful for converting drugs derivatized with 13-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

The enzymes of the present invention can be covalently bound to the antibody by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984)).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol.

The antibodies disclosed herein may also be formulated as liposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. J; Biol. Chem. 257: 286-288 (1982) via a disulfide interchange reaction. A chemotherapeutic agent is optionally contained within the liposome (See Gabizon et al. ANational Cancer Inst. 81 (19) 1484 (1989)).

Amino acid sequence modifications of antibodies described herein are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter posttranslational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide which increases the serum half-life of the antibody.

Another type of variant is an amino acid substitution variant. These variants have at least one amino acid residue in the antibody molecule replaced by different residue. The sites of greatest interest for substitutional mutagenesis of antibody include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Naturally occurring residues are divided into groups based on common side-chain properties:

(1) hydrophobic: norleucine, met, ala, val, leu, ile;
(2) neutral hydrophiuic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bonds may be added to the antibody to improve its stability (particularly where the antibody is a fragment such as an Fv fragment).

A particularly preferred type of substitutional variant involves substituting one or more hypervariable region residues of a parent antibody (e.g. a humanized or human antibody). Generally, the resulting variants selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibodies used in the present invention to improve effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J Iimmunol 148: 2918-2922 (1992).

Homodimeric antibodies with enhanced anti-tumor activity may also be prepared using heterobifunctional cross-linkers as described in Wolff et al. Cancer Research 53: 2560-2565 (1993). Alternatively, an antibody can be engineered which has dual Fc regions and may thereby have enhanced complement lysis and ADCC capabilities (See Stevenson et al. Anti-CancerDrugDesign 3: 2 19-230 (1989)).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Diagnosing a Disease Associated with CDH3

The antibodies of the present invention may be used as a marker for diagnosing a disease that is associated with CDH3 such as cancer.

More specifically, by detecting the CDH3 polypeptide with the antibody of the present invention in a subject-derived sample, a disease associated with CDH3 can be diagnosed. Thus, the present invention provides methods for diagnosing a disease associated with CDH3 or a predisposition for developing the disease in a subject by detecting the CDH3 polypeptide with the antibody of the present invention in the subject-derived sample. The methods comprise the steps of:

(a) contacting a sample or a specimen from the subject with the antibody or the fragment thereof of the present invention;
(b) detecting the CDH3 polypeptide in the sample or specimen; and
(c) judging whether or not the subject suffers from or is at risk of developing the disease based on the relative abundance of the CDH3 protein compared to a control.

In a typical embodiment, a disease associated with CDH3 is cancer, more specifically, pancreatic, lung, colon, prostate, breast, gastric or liver cancer.

Alternatively, in a other embodiments, the antibody of the present invention may be used for detecting or imaging a cancer in a living body. More specifically, the present invention provides methods of detecting or imaging a cancer which comprise the steps of:

(1) administering to a subject the antibody or fragment thereof of the present invention;
(2) detecting accumulation or localization of the antibody or the fragment in a living body, and
(3) determining the location of the antibody or the fragment, within the subject.

Alternatively, according to the present invention, cancer cells or tissues may be detected in a subject. For example, the present invention provides methods for detecting a cancer, in which CDH3 is expressed, in a subject, comprising: administering the antibody or fragment thereof of the present invention to the subject allowing the antibody or fragment specifically binds to CDH3 polypeptide in subject cells or tissue; visualizing the antibody bound in the cells or tissue; and comparing the level of the antibody bound to the cells or tissue to a normal control cells or tissue, wherein an increase in the level of the antibody bound to the subject cells or tissue relative to the normal control cells or tissue is indicative of a cancer in the subject.

Preferably, in order to trace the antibody administered into a living body, the antibody may be labeled with detectable molecules. For example, the behavior of antibodies labeled with a fluorescent substance, luminescent substance, or radioisotope can be traced in vivo. Methods for labeling an antibody with such molecules are well known in the art.

Antibodies labeled with a fluorescent substance or a luminescent substance can be observed, for example, using an endoscope or a laparoscope. When using a radioisotope, the localization of an antibody can be imaged by tracing the radioactivity of the radioisotope. In the present invention, the localization or accumulation of the antibody of the present invention in vivo demonstrates the presence of cancer cells.

Similar methods have been employed for other antibodies, and the skilled practitioner will be aware of the various methods suitable for imaging the location of detectably bound antibody or fragments within the body. As a nonlimiting guide, about 10-1000 microgram (mcg.), preferably about 50-500 mcg, more preferably about 100-300 mcg, more preferably about 200-300 mcg of purified antibody are administered. For example, applicable doses for humans include about 100-200 mcg/kg body weight, or 350-700 mg/m$^2$ of body-surface area.

Kits for Diagnosing a Disease Associated with CDH3

The present invention provides a kit for diagnosis of a disease associated with CDH3. Specifically, the kit includes the antibody or fragment thereof of the present invention as a detection regent for CDH3 polypeptide. In an embodiment, the antibody for the kit of the present invention may be labeled with fluorescent substance, luminescent substance, or radioisotope. Methods for labeling antibodies and detecting the labeled antibodies are well known in the art and any labels and methods may be employed for the present invention.

Furthermore, the kit may include positive and negative control reagents, and a secondary antibody for detecting the antibody of the present invention. For example, tissue samples obtained from healthy normal subjects or noncancerous tissues may serve as useful negative control reagents. The kit of the present invention may further include other materials desirable from a commercial and user standpoint, including buffers, diluents, filters, needles, syringes, and package inserts (e.g., written, tape, CDROM, etc.) with instructions for use. These reagents and such may be retained in a container with a label. Suitable containers include bottles, vials, and test tubes. The containers may be formed from a variety of materials, such as glass or plastic.

In other embodiments, the present invention further provides a kit for use in detecting, imaging or treating a cancer within a subject to be diagnosed comprising the antibody of the present invention. Alternatively, the present invention also provides a diagnostic agent comprising the antibody of the present invention, so that the agent is used for administration into a subject to be diagnosed for a disease associated with CDH3, including a cancer. In preferable embodiments, the antibody of the present invention may be labeled with a radioisotope. For example, the kit of the present invention may contain the antibody of the present invention modified with chelating agent and radioactive substance. MX-DOPA is preferable chelating agent for modifying the antibody. Meanwhile, indium-111 ($^{111}$In) can be used as a tracer for bioimaging. Alternatively, in order for radioimmunotherapy of a disease associated with CDH3, the antibody may be labeled with beta nuclides e.g. Yttrium-90 ($^{90}$Y). In the present invention, indium-111 ($^{111}$In) or Yttrium-90 ($^{90}$Y) may also be provided as salt or solution thereof. Suitable salt of indium-111 ($^{111}$In) or Yttrium-90 ($^{90}$Y) is chloride.

In a preferable embodiment, a disease associated with CDH3 is pancreatic, lung, colon, prostate, breast, gastric or liver cancers.

Therapeutic Uses

Described below are methods and pharmaceutical compositions for treating and/or preventing a disease associated with CDH3, or inhibiting CDH3-expressing cell growth using the antibody of the present invention. In typical embodiment, a disease associated with CDH3 is cancer, including but not limited to a pancreatic, lung, colon, prostate, breast, gastric or liver cancer cell. Specifically, the method for treating and/or preventing a disease associated with CDH3, or inhibiting CDH3-expressing cell growth, in a subject according to the present invention comprises administering to the subject an effective amount of the antibody or fragment thereof of the present invention.

The subject in the present invention may be animals including mammals and avian animals. For example, mammals may include humans, mice, rats, monkeys, rabbits, and dogs.

The antibody or fragment thereof described herein can specifically bind to CDH3 polypeptide, so when the antibody or fragment thereof are administered to a subject, it binds to CDH3 polypeptide in the subject and may suppress CDH3-expressing cell growth such as cancerous cells. Alternatively, when the antibody or fragment thereof may be conjugated with a therapeutic moiety and administered to a subject, it is delivered to a region that expresses CDH3 polypeptide (i.e. suffered region) in a subject and the therapeutic moiety can be selectively delivered to the suffered region and acted thereon. Such therapeutic moiety may be any therapeutics that are known or will be developed for having a therapeutic efficacy on the cancer and includes, but not limited to, a radioisotope label and chemotherapeutic agent. A radioisotope label which can be used as therapeutics can be selected depending on a variety of elements including beta-ray energy and its emission efficiency, the presence or absence of gamma-ray emitted, its energy and emission efficiency, physical half-life, and labeling procedure. Generally, the radioisotope label based on yttrium (such as $^{90}$Y) and iodine (such as $^{125}$I and $^{131}$I) may be used. A chemotherapeutic agent may be any agent that is known or will be developed for treating the cancer and includes, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel. The antibody or fragment thereof of the present invention can selectively bind to CDH3 polypeptide and not bind to a normal cell, so side effect which is caused by the antibody or fragment thereof, or radioisotope or chemotherapeutic agent can be effectively avoided and therefore the therapeutic potency may be high.

The antibody or fragment thereof described herein can be administered to a subject at effective doses to treat or prevent a CDH3-associated disease. An effective dose refers to that amount of the antibody or a fragment thereof sufficient to result in a healthful benefit in the treated subject. Formulations and methods of administration that can be employed when the pharmaceutical composition contains the antibody or fragment thereof of the present invention are described below.

It is to be further understood that a cocktail of different monoclonal antibodies, such as a mixture of the specific monoclonal antibodies described herein or fragments, may be administered, if necessary or desired, to alleviate diseases associated with CDH3. Indeed, using a mixture of monoclonal antibodies, or fragments thereof, in a cocktail to target several antigens, or different epitopes, on disease cells, is an advantageous approach, particularly to prevent evasion of tumor cells and/or cancer cells due to downregulation of one of the antigens.

Pharmaceutical compositions for use in accordance with the present invention can be formulated in conventional manner using one or more pharmaceutically acceptable carriers or excipients. Thus, the present invention provides pharmaceutical compositions for treating or preventing a disease associated with CDH3, or inhibiting CDH3-expressing cell growth, comprising an effective amount of the antibody or fragment thereof of the present invention, and pharmaceutically acceptable carriers or excipients.

The antibodies or fragments thereof can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the antibody can be in lyophilized powder form for constitution with a suitable vehicle, e.g., sterile pyrogen-free water, before use.

Toxicity and therapeutic efficacy of the antibody or fragment, or the therapeutic moiety conjugated thereto can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD/ED.

The data obtained from the cell culture assays and animal studies can be used in formulating a range of dosages for use in humans. The dosage of the antibodies lies preferably within a range of circulating plasma concentrations that include the ED50 with little or no toxicity. The dosage can vary within this range depending upon the dosage form employed, the route of administration utilized and types and amounts of the therapeutic moiety conjugated. For the antibody or fragment thereof of the present invention, the effective dose can be estimated initially from cell culture assays. A dose can be formulated in animal models to achieve a circulating plasma concentration range that includes the IC50 (i.e., the concentration of the test antibody that achieves a half-maximal inhibition of symptoms) as determined in cell culture. Such information can be used to more accurately determine useful doses in humans. Levels in plasma can be measured, for example, by high performance liquid chromatography.

While depending on the conditions and age of the subject and/or administration route, one skilled in the art can select an appropriate dose of the pharmaceutical composition of the present invention. For example, the pharmaceutical composition of the present invention is administered in an amount such that the antibody according to the present invention is administered to the subject in a day in an amount of about 3 to about 15 mcg per kg body weight of subject, and preferably of about 10 to about 15 mcg per kg body weight of subject. The administration interval and times can be selected in consideration of the condition and age of the subject, administration route, and response to the pharmaceutical composition. For example, the pharmaceutical composition can be administered to the subject one to 5 times, preferably 1 times a day for 5 to 10 days.

In another aspect, when the composition comprising the radioisotope labeled antibody is parenterally administered, the administrative dose for a single adult is 0.1 mCi/kg to 1.0 mCi/kg, preferably 0.1 mCi/kg to 0.5 mCi/kg, and more preferably 0.4 mCi/kg at once.

The pharmaceutical composition can be administered systemically or locally. It is preferably administered in a targeting delivery manner so as to deliver the active component to an affected site.

In particular embodiments, the methods and compositions of the present invention are used for the treatment or prevention of the cancer together with one or a combination of chemotherapeutic agents including, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel.

With respect to radiation therapy, any radiation therapy protocol can be used depending upon the type of the cancer to be treated. For example, but not by way of limitation, X-ray radiation can be administered. Gamma ray emitting radioisotopes, such as radioactive isotopes of radium, cobalt, and other elements may also be administered to expose tissues.

In another embodiment, chemotherapy or radiation therapy is administered, preferably at least an hour, five hours, 12 hours, a day, a week, a month, and more preferably several months (e.g., up to three months) subsequent to using the methods and compositions containing the antibody of the present invention. The chemotherapy or radiation therapy administered prior to, concurrently with, or subsequent to the treatment using the methods and compositions according to the present invention can be administered by any method known in the art.

In another embodiment, the present invention also provides the use of the antibody of the present invention in manufacturing a pharmaceutical composition for treating or preventing a disease associated with CDH3. In particular, the present invention further provides a use of radio-labeled antibody of the present invention for manufacturing a pharmaceutical composition for treating or preventing a cancer.

Alternatively, the present invention further provides the antibody of the present invention for use in treating or preventing a disease associated with CDH3. In particular, the radio-labeled antibody of the present invention for use in radioimmunotherapy for cancer is also provided.

Alternatively, the present invention further provides a method or process for manufacturing a pharmaceutical composition for treating or preventing a disease associated with CDH3, wherein the method or process comprises step for formulating a pharmaceutically or physiologically acceptable carrier with the antibody of the present invention as active ingredients. In particular, the present invention further provides a method or process for manufacturing a pharmaceutical composition for treating or preventing a cancer, wherein the method or process comprises step for formulating a pharmaceutically or physiologically acceptable carrier with the radio-labeled antibody of the present invention as active ingredients.

In another embodiment, the present invention also provides a method or process for manufacturing a pharmaceutical composition for treating or preventing a disease associated with CDH3, wherein the method or process comprises step for admixing an active ingredient with a pharmaceutically or physiologically acceptable carrier, wherein the active ingredient is the antibody of the present invention. In particular, the present invention further provides a method or process for manufacturing a pharmaceutical composition for treating or preventing a cancer, wherein the method or process comprises step for admixing the radio-labeled antibody of the present invention with a pharmaceutically or physiologically acceptable carrier.

In further embodiment, the present invention provides the antibody of the present invention for use in bioimaging or immunoscintigraphy for cancer within a subject to be diagnosed. Alternatively, the present invention provides use of the antibody of the present invention for manufacturing a diagnostic agent for bioimaging or immunoscintigraphy for cancer within a subject. The present invention further provides a method or process for manufacturing a diagnostic agent for bioimaging or immunoscintigraphy for cancer within a subject, wherein the method or process comprises step for admixing the antibody of the present invention with a pharmaceutically or physiologically acceptable carrier.

All prior art references cited herein are incorporated by reference in their entirety.

EXAMPLES

Below, the present invention is further explained based on Examples.

Materials and Methods

Antibody Production.

CDH3 gene encoded extracellular domain (SEQ ID NO: 83) was amplified from cDNA pool derived from cancer cells. The product was cloned into the pcDNA3.1 (Invitrogen, CA). To produce CDH3-specific antibody, mice were immunized subcutaneously with the domain expression vector (17.5 micro g/injection) every two weeks for a month. After the confirmation of the titer of antisera, splenocytes were extracted from the mice and fused to myeloma cells to prepare hybridomas. Hybridomas which can produce an antibody binding to native CDH3 antigen on the surface of the cancer cells were screened. Through the screening, hybridoma clone #3, clone #4, clone #5 and clone #6 were confirmed to produce antigen-specific antibody at high level, therefore these hybridomas were selected to produce antibody for further experiments. The hybridoma clone #3, clone #4, clone #5 and clone #6 were injected intraperitoneally into mice, and the ascites were recovered after 2 to 3 weeks. The antibodies were purified from the ascites using Protein A column (GE Healthcare, NJ). Herein, antibodies are also referred to as clone #3, clone #4, clone #4 and clone #6.

Cell Culture.

H1373, human non-small cell lung cancer line, was used for the therapeutic study in vivo since it was confirmed to express CDH3 polypeptide. H1373 was purchased from American Type Culture Collection (Manassasm, Va.), and was maintained in RPMI supplemented with 10% fetal bovine serum (FBS) and 1% penicillin/streptomycin at 37 degrees C. in a humidified atmosphere of 5% $CO_2$.

Radiolabeling.

Anti-CDH3 mouse monoclonal antibodies produced by hybridoma clone #3, clone #4, clone #5, clone #6 and control antibody, which was normal mouse IgG1 (Nordic immunological laboratories, Tiburg, The Netherlands), were labeled with Yttrium-90 (90Y). Antibody was labeled with 90Y via a bifunctional metal ion chelating agent, pSCN-Bn-DTPA (Macrocyclics, Dallas, Tex., USA). One milligram of the antibody was conjugated to that chelator in dimethylformamide at a molar ratio of 1:5, respectively. After incubation at 37 degrees C. for 20 hours, antibody-chelator complexes were purified using Biospin Column 6 (Bio-Rad, Tokyo, Japan). 90YCl$_3$ (QSA Global, Brauschweig, Germany) was pre-incubated with 0.25 M acetic acid (pH5.5) for 5 minutes at room temperature in parallel. To obtain 90Y-labeled antibodies, the antibody-chelator complex was incubated with the preincubated 90YCl$_3$ solution at 37 degrees C. for 1 hour, respectively. Labeled antibody was purified using Biospin Column 6 according to manufacture's instructions. During labeling processes, degradation of these antibodies was not observed.

Xenograft Models.

Animal care and treatment was performed in accordance with the guidelines of animal use and animal committee of the Gunma University. 100 microliter of H1373 cell suspension (1×107 cells) was inoculated subcutaneously into the right flank of female 3- to 5-week-old nude mice (Charles River Laboratories Japan Inc. Yokohama, Japan). These mice were kept for several weeks to develop the tumors. The established tumors were isolated from tumor-bearing mice and dissected into cubic tissue fragments 2 mm on a side. These fragments were transplanted serially into nude mice. After the transplantation, these mice were kept until the average tumor volume reached 100 mm$^3$.

Radiotherapy.

Xenograft mice were randomly assigned to ten different treatment groups. 90Y-labeled antibodies (4-10 mCi/mg) were prepared as described above. The mice were injected intravenously with 90Y-labeled or non-labeled clone #3, clone #4, clone #5 or clone #6. 90Y-labeled normal mouse IgG1 was injected as control. Radioactivity of injected antibodies was adjusted to 100 microCi per animal. Body weight and tumor volume of the treated-xenograft mice were monitored for 5 weeks after injection. The tumor volume (mm$^3$) was calculated using following formula: (the shortest diameter)$^2$×(the longest diameter)×0.5.

Reduced SDS-PAGE.

Each 5 micro-g of anti-CDH3 antibody was mixed with SDS buffer that included 4% SDS, 125 mM Tris-HCl (pH6.8), 20% glycerol, 0.04% Bromophenol Blue and 10% mercaptoethanol. After heated, the mixtures were applied to 4-20% gradient SDS-PAGE gel. Then, the gel was stained with Coomassie brilliant blue R-250 (CBB) and destained by using 10% methanol and 7% acetic acid. An image of the gel was captured by scanner.

Analysis for Amino Acid Sequence of Variable Region.

Total RNAs were extracted from hybridoma clone #3, clone #4 and clone #5 using RNeasy Mini Kit (QIAGEN). The cDNAs were synthesized from the total RNAs using SuperScript II Reverse Transcriptase (Invitrogen). The polynucleotides encoding variable regions of monoclonal antibodies were amplified using NovaTaq DNA polymerase (Novagen) and Mouse Ig-Primer Set (Novagen). The primers for amplification are follows:

```
MuIgVH5'-B;
                                         (SEQ ID NO: 84)
5'-GGGAATTCATGRAATGSASCTGGGTYWTYCTCTT-3'
for heavy chain 5' primer, MuIg kappa VL5'-D (mixture of following primers);
                                         (SEQ ID NO: 85)
5'-ACTAGTCGACATGAGGRCCCCTGCTCAGWTTYTTGGIWTCTT-3'
and (SEQ ID NO: 86)
5'-ACTAGTCGACATGGGCWTCAAGATGRAGTCACAKWYYCWGG-3'
for light chain 5' primer, MuIgGVH3'-2;
                                         (SEQ ID NO: 87)
5'-CCCAAGCTTCCAGGGRCCARKGGATARACIGRTGG-3'
for heavy chain 5' primer, and MuIg kappa VL3'-1;
                                         (SEQ ID NO: 88)
5'-CCCAAGCTTACTGGATGGTGGGAAGATGGA-3'
for light chain 3' primer.
```

PCR products were cloned into pCR2.1-TOPO (Invitrogen). Insert regions were sequenced and the nucleic acid sequences of the variable regions (except for the signal sequence) of clone #3, clone #4 and clone #5 were determined.

Following symbols are used for the different nucleotides in the primer sequences;

B as C, G or T, D as A, G or T, H as A, C or T, I as inosine, K as G or T, M as A or C, R as A or G, S as C or G, V as A, C or G, W as A or T and Y as C or T.

Results.

To evaluate the efficacy of CDH3 targeted radioimmunotherapy, anti-CDH3 antibodies were radiolabeled with beta-emitting isotope $^{90}$Y (t1/2=64.1 hours), and administered by intravenous injection to tumor-bearing nude mice. The growth rate of tumors treated with yttrium-90 labeled clone #3, #4 and #6 were drastically decreased by radiation from yttrium-90 conjugated with the antibodies (FIG. 1). In particular, 90Y-labeled clone #3 and clone #6 strongly suppressed tumor growth in H1373 xenograft mice during observation. On the other hand, $^{90}$Y-labeled control antibody showed no effect on tumor growth. Therefore, therapeutic effects of $^{90}$Y-labeled antibodies seemed to depend on its affinities to CDH3 polypeptide, which was expressed on tumor cell surface. The body weights of mice treated with any antibodies did not significantly decrease (data not shown).

Anti-CDH3 antibody clone #3, clone #4 and clone #6 conjugated yttrium-90 exerted remarkable therapeutic effects against tumor. Therefore, CDH3 would be an attractive target for cancer therapy and anti-CDH3 antibody would be available as a novel tool for cancer therapy.

The amino acid sequences of H chain V regions and L chain Variable regions of mouse monoclonal antibodies were determined as follows:

```
clone #3, H chain variable region
(except for the signal sequence):
                                          (SEQ ID NO: 4)
QVQLQQPGAELVRPGSSVKLSCKASGYTFTSFWIHWVKQRPMQGLEWIGN

IDPSDSETHYNQYFKDRATLTVDRSSSTAYMHLTSLTSEDSAVYYCARGG

TGFSSWGQGTLVTVSA
(encoded by the nucleic acid sequence shown in
SEQ ID NO: 3);

clone #3, L chain variable region
(except for the signal sequence):
                                          (SEQ ID NO: 12)
DIKMTQSPSSMYASLGERVTITCKASQDIDSYLSWFQQKPGKSPKTLIHR

ANRLVDGVPSRFSGSGSGQDYSLTISSLEYEDMGIYYCLQYDEFPRTFGG

GTKLEIK
(encoded by the nucleic acid sequence shown in
SEQ ID NO: 11);

clone #4, H chain variable region
(except for the signal sequence):
                                          (SEQ ID NO: 20)
LVQLQQPGAELVRPGSSVKLSCKTSGYTFTSYWMHWIKQRPIQGLEWIGN

IDPSDSETHYNQNFNDRATFTVDKSSSTAYMELSSLTSEDSAVYYCARGG

TGFAYWGQGTLVTVSA
(encoded by the nucleic acid sequence shown in
SEQ ID NO: 19);

clone #4, L chain variable region
(except for the signal sequence):
                                          (SEQ ID NO: 28)
DIKMTQSPSSMYASLGERVTITCKASQDINNYLGWFQQKPGKSPKTLIHR

TDRLIEGVPSRFSGSGSGQDYSLTISSLEYEDVGTYYCLQYDEFPRMFGG

GTKLEIK
(encoded by the nucleic acid sequence shown in
SEQ ID NO: 27);

Clone #5, H chain variable region
(except for the signal sequence):
                                          (SEQ ID NO: 36)
LVQLQQPGAELVRPGSSVKLSCKASGYTFTSYWMHWIKQRPIQGLEWIGN

IDPSDSETHYNQKFNDRARLTVDKSSSTAYMHLSSLTSEDSAVYYCARGG

TGFAYWGQGTLVTVSA
(encoded by the nucleic acid sequence shown in
SEQ ID NO: 35); and clone #5, L chain variable region
(except for the signal sequence):
                                          (SEQ ID NO: 44)
DIKMTQSPSSMYASLGERVTITCKASQDINNYLGWFQQKPGKSPKTLIHR

TDRLIEGVPSRFSGSGSGQDYSLTISSLEYEDVGTYYCLQYDEFPRMFGG

GTKLDIK
(encoded by the nucleic acid sequence shown in
SEQ ID NO: 43).
```

The CDR sequences of the antibodies determined by the Kabat definition are as follows:

clone #3, SFWIH (SEQ ID NO: 6) (encoded by the nucleic acid sequence shown in SEQ ID NO: 5) as VH CDR1, NIDPSDSETHYNQYFKD (SEQ ID NO: 8) (encoded by the nucleic acid sequence shown in SEQ ID NO: 7) as VH CDR2 and GGTGFSS (SEQ ID NO: 10) (encoded by the nucleic acid sequence shown in SEQ ID NO: 9) as VH CDR3, KASQDIDSYLS (SEQ ID NO: 14) (encoded by the nucleic acid sequence shown in SEQ ID NO: 13) as VL CDR1, RANRLVD (SEQ ID NO: 16) (encoded by the nucleic acid sequence shown in SEQ ID NO: 15) as VL CDR2 and LQYDEFPRT (SEQ ID NO: 18) (encoded by the nucleic acid sequence shown in SEQ ID NO: 17) as VL CDR3;

clone #4, SYWMH (SEQ ID NO: 22) (encoded by the nucleic acid sequence shown in SEQ ID NO: 21) as VH CDR1, NIDPSDSETHYNQNFND (SEQ ID NO: 24) (encoded by the nucleic acid sequence shown in SEQ ID NO: 23) as VH CDR2 and GGTGFAY (SEQ ID NO: 26) (encoded by the nucleic acid sequence shown in SEQ ID NO: 25) as VH CDR3, KASQDINNYLG (SEQ ID NO: 30) (encoded by the nucleic acid sequence shown in SEQ ID NO: 29) as VL CDR1, RTDRLIE (SEQ ID NO: 32) (encoded by the nucleic acid sequence shown in SEQ ID NO: 31) as VL CDR2 and LQYDEFPRM (SEQ ID NO: 34) (encoded by the nucleic acid sequence shown in SEQ ID NO: 33) as VL CDR3; and clone #5, SYWMH (SEQ ID NO: 38) (encoded by the nucleic acid sequence shown in SEQ ID NO: 37) as VH CDR1, NIDPSDSETHYNQKFNDRA (SEQ ID NO: 40) (encoded by the nucleic acid sequence shown in SEQ ID NO: 39) as VH CDR2 and GGTGFAY (SEQ ID NO: 42) (encoded by the nucleic acid sequence shown in SEQ ID NO: 41) as VH CDR3, KASQDINNYLG (SEQ ID NO: 46) (encoded by the nucleic acid sequence shown in SEQ ID NO: 45) as VL CDR1, RTDRLIE (SEQ ID NO: 48) (encoded by the nucleic acid sequence shown in SEQ ID NO: 47) as VL CDR2 and LQYDEFPRM (SEQ ID NO: 50) (encoded by the nucleic acid sequence shown in SEQ ID NO: 49) as VL CDR3.

Figure 2:
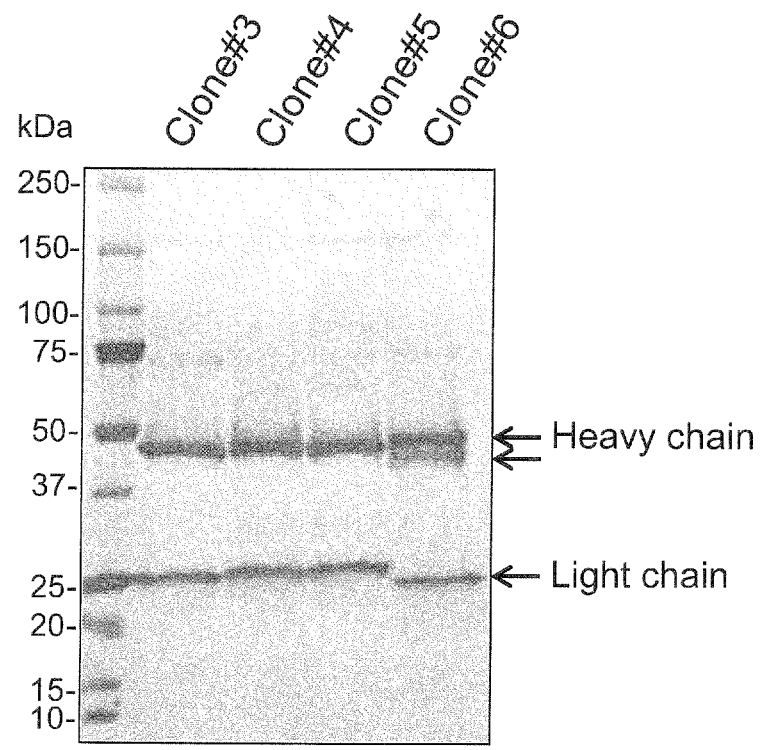
FIG. 2 shows reduced SDS-PAGE analysis of anti-CDH3 antibodies (clone #3, #4, #5 and #6). Banding pattern of clone #3, #4 and #5 revealed two bands corresponding to IgG heavy chain and light chain, while that of clone #6 revealed two heavy chain bands and single light chain band.

SDS-PAGE analysis was performed under reducing condition. The band patterns on the gel were characterized by molecular weight range 40-50 kDa which corresponding to IgG heavy chain and lower molecular weight ranges of 20-30 kDa which correspond to IgG light chain. Anti-CDR3 antibody clone #3, clone #4 and clone #5 exhibited single heavy chain band and single light chain band as general IgG. On the other hand, anti-CDR3 antibody clone #6 showed two heavy chain bands and single light chain band. Incomplete glycosylation at variable region of heavy chain caused to the additional heavy chain band during reduced SDS-PAGE. As shown in FIG. 2, incomplete glycosylation affects uniformity of the antibody, and it may create difficulty in development of therapeutic drugs. Therefore, variants of clone #6 which have a single amino acid substitution at glycosylation site of clone #6 were designed in order to avoid glycosylation in H chain variable region. These variants would be more applicable for development of antibody-based cancer drug than clone #6.

The amino acid sequences of H chain variable regions of clone #6 variants are as follows (underline indicates a substituted amino acid residue):

```
clone #6NS, H-chain variable region
(except for the signal sequence):
                                          (SEQ ID NO: 68)
QVQLQQPGAELVKPGTSVKLSCKSSGYTFTSYWIHWVKQRPGHGLEWIGE

IDPSDSYTYYNQNFKGKATLTIDKSSSTAYMQLNSLTSEDSAVFYCARSG

YGNLFVYWGQGTLVTVSA
(encoded by the nucleic acid sequence shown in
SEQ ID NO: 67);

clone #6NT, H-chain variable region
(except for the signal sequence):
                                          (SEQ ID NO: 72)
QVQLQQPGAELVKPGTSVKLSCKSSGYTFTSYWIHWVKQRPGHGLEWIGE

IDPSDTYTYYNQNFKGKATLTIDKSSSTAYMQLNSLTSEDSAVFYCARSG

YGNLFVYWGQGTLVTVSA
(encoded by the nucleic acid sequence shown in
SEQ ID NO: 71);

clone #6NA, H-chain variable region
(except for the signal sequence):
                                          (SEQ ID NO: 76)
QVQLQQPGAELVKPGTSVKLSCKSSGYTFTSYWIHWVKQRPGHGLEWIGE

IDPSDAYTYYNQNFKGKATLTIDKSSSTAYMQLNSLTSEDSAVFYCARSG

YGNLFVYWGQGTLVTVSA
(encoded by the nucleic acid sequence shown in
SEQ ID NO: 75); and -continued
clone #6NQ, H-chain variable region
(except for the signal sequence):
                                          (SEQ ID NO: 80)
QVQLQQPGAELVKPGTSVKLSCKSSGYTFTSYWIHWVKQRPGHGLEWIGE

IDPSDQYTYYNQNFKGKATLTIDKSSSTAYMQLNSLTSEDSAVFYCARSG

YGNLFVYWGQGTLVTVSA
(encoded by the nucleic acid sequence shown in
SEQ ID NO: 79).
```

The amino acid sequences of L chain variable regions (except for the signal sequence) of clone #6 variants are the same as that of clone #6;

```
                                          (SEQ ID NO: 60)
QIVLTQSPAIMSSSPGEKVTMSCSATSSVTYMYWYQQKPGSSPKPWIFRT

SNLASGVPTRFSGSGSGTSYSLTISSMEAEDAATYYCQHYHIYPRTFGGG

TKLEIK
(encoded by the nucleic acid sequence shown in
SEQ ID NO: 59).
```

The VH CDR2 sequences determined by the Kabat definition of the clone #6 variants are; EIDPSDSYTYYNQNFKG (SEQ ID NO: 70) (encoded by the nucleic acid sequence shown in SEQ ID NO: 69) for clone #6NS, EIDPSDTYTYYNQNFKG (SEQ ID NO: 74) (encoded by the nucleic acid sequence shown in SEQ ID NO: 73) for clone #6NT, EIDPSDAYTYYNQNFKG (SEQ ID NO: 78) (encoded by the nucleic acid sequence shown in SEQ ID NO: 77) for clone #6NA, and EIDPSDQYTYYNQNFKG (SEQ ID NO: 82) (encoded by the nucleic acid sequence shown in SEQ ID NO: 81) for clone #6NQ.

The other CDR sequences determined by the Kabat definition of the variants are the same as those of clone #6; SYWIH (SEQ ID NO: 54) (encoded by the nucleic acid sequence shown in SEQ ID NO: 53) as VH CDR1, SGYGNLFVY (SEQ ID NO: 58) (encoded by the nucleic acid sequence shown in SEQ ID NO: 57) as VH CDR3, SATSSVTYMY (SEQ ID NO: 62) (encoded by the nucleic acid sequence shown in SEQ ID NO: 61) as VL CDR1, RTSNLAS (SEQ ID NO: 64) (encoded by the nucleic acid sequence shown in SEQ ID NO: 63) as VL CDR2 and QHYHIYPRT (SEQ ID NO: 66) (encoded by the nucleic acid sequence shown in SEQ ID NO: 65) as VL CDR3.

INDUSTRIAL APPLICABILITY

The present invention is based, at least in part, on the discovery that a cancer expressing CDH3 can be treated with radioisotope labeled anti-CDH3 antibody in vivo. CDH3 was reported as a gene strongly expressed in pancreatic, lung, colon, prostate, breast, gastric or liver cancers. Thus, treatment of a cancer, for example, pancreatic, lung, colon, prostate, breast, gastric or liver cancer is conveniently carried out using anti-CDH3 antibodies labeled with radioisotope label.

The invention claimed is:

1. An antibody or an antigen binding fragment thereof, wherein the antibody comprises an H (heavy) chain V (variable) region and an L (light) chain V region, wherein the H chain V region and the L chain V region selected from the group consisting of:
   (a) an H chain V region comprising complementarity determining regions (CDRs) included in an H chain V region having the amino acid sequence shown in SEQ ID NO: 4, and an L chain V region comprising CDRs included in an L chain V region having the amino acid sequence shown in SEQ ID NO 12;
   (b) an H chain V region comprising CDRs included in an H chain V region having the amino acid sequence shown in SEQ ID NO: 20, and an L chain V region comprising CDRs included in an L chain V region having the amino acid sequence shown in SEQ ID NO: 28; and
   (c) an H chain V region comprising CDRs included in an H chain V region having the amino acid sequence shown in SEQ ID NOs: 68, 72, 76 or 80, and an L chain V region comprising CDRs included in an L chain V region having the amino acid sequence shown in SEQ ID NO: 60, and wherein the antibody is capable of binding to a CDH3 polypeptide or a partial peptide thereof.

2. The antibody or an antigen binding fragment thereof according to claim 1, wherein the H chain V region and the L chain V region selected from the group consisting of:
   (a) an H chain V region comprising CDR1 having the amino acid sequence shown in SEQ ID NO: 6, CDR2 having the amino acid sequence shown in SEQ ID NO: 8 and CDR3 having the amino acid sequence shown in SEQ ID NO: 10, and an L chain V region comprising CDR1 having the amino acid sequence shown in SEQ ID NO: 14, CDR2 having the amino acid sequence shown in SEQ ID NO: 16 and CDR3 having the amino acid sequence shown in SEQ ID NO: 18;
   (b) an H chain V region comprising CDR1 having the amino acid sequence shown in SEQ ID NO: 22, CDR2 having the amino acid sequence shown in SEQ ID NO: 24 and CDR3 having the amino acid sequence shown in SEQ ID NO: 26, and an L chain V region comprising CDR1 having the amino acid sequence shown in SEQ ID NO: 30, CDR2 having the amino acid sequence shown in SEQ ID NO: 32 and CDR3 having the amino acid sequence shown in SEQ ID NO: 34; and
   (c) an H chain V region comprising CDR1 having the amino acid sequence shown in SEQ ID NO: 54, CDR2 having the amino acid sequence shown in SEQ ID NOs: 70, 74, 78 or 82 and CDR3 having the amino acid sequence shown in SEQ ID NO: 58, and an L chain V region comprising CDR1 having the amino acid sequence shown in SEQ ID NO: 62, CDR2 having the amino acid sequence shown in SEQ ID NO: 64 and CDR3 having the amino acid sequence shown in SEQ ID NO: 66.

3. The antibody or fragment thereof according to claim 1, wherein the antibody is selected from the group consisting of a mouse antibody, a chimeric antibody, a humanized antibody, an antibody fragment, and single-chain antibody.

4. The antibody or fragment thereof according to claim 3, wherein the antibody comprises an H chain V region having the amino acid sequence selected from the group consisting of SEQ ID NOs: 4, 20, 68, 72, 76 and 80 and an L chain V region having the amino acid sequence selected from the group consisting of SEQ ID NOs: 12, 28 and 60.

5. The antibody or fragment thereof according to claim 4, wherein the antibody comprises:
   (a) an H chain V region having the amino acid sequence shown in SEQ ID NO: 4 and an L chain V region having the amino acid sequence shown in SEQ ID NO: 12;
   (b) an H chain V region having the amino acid sequence shown in SEQ ID NO: 20 and an L chain V region having the amino acid sequence shown in SEQ ID NO: 28; or
   (c) an H chain V region having the amino acid sequence shown in SEQ ID NOs: 68, 72, 76 or 80 and an L chain V region having the amino acid sequence shown in SEQ ID NO: 60.

6. The antibody or fragment thereof according to claim 4, wherein the antibody is chimeric antibody.

7. The antibody or fragment thereof according to claim 6, wherein the antibody is a humanized antibody.

8. The antibody or fragment thereof according to claim 7, wherein the humanized antibody further comprises a human antibody FR (framework) region and/or a human antibody C region.

9. The antibody or fragment thereof according to claim 1, wherein the antibody is conjugated with a cytotoxic, a therapeutic agent, a radioisotope label or a fluorescent label.

10. The antibody or fragment thereof according to claim 9, wherein the radioisotope label is selected from 90yttrium ($^{90}Y$) and 111indium ($^{111}In$).

11. A method for treating a cancer expressing CDH3, or inhibiting CDH3-expressing cancer cell growth, in a subject, wherein the method comprises administering to the subject an effective amount of the antibody or fragment according to claim 1, wherein the antibody or fragment is conjugated with a cytotoxic label.

12. A method for diagnosis of a cancer expressing CDH3 or of a predisposition to develop the cancer in a subject, wherein the cancer is selected from the group consisting of pancreatic, lung, colon, prostate, breast, gastric and liver cancers, and wherein the method comprises:
   (a) contacting a sample or a specimen from the subject with the antibody or fragment according to claim 1;
   (b) detecting a CDH3 polypeptide in the sample or specimen by detecting said antibody or fragment; and
   (c) judging whether or not the subject suffers from or is at risk of developing the disease based on the relative abundance of the CDH3 polypeptide compared to a control, wherein an increase of the CDH3 polypeptide compared to the control is indicative that the subject is suffering or is at risk of developing said cancer.

13. A pharmaceutical composition for treating a cancer expressing CDH3, or inhibiting CDH3-expressing cancer cell growth, wherein the pharmaceutical composition comprises an effective amount of the antibody or fragment according to claim 1 and a pharmaceutically acceptable carrier or excipient, wherein the antibody or fragment is conjugated with a cytotoxic label.

14. A kit for diagnosis of a cancer expressing CDH3 selected from the group consisting of pancreatic, lung, colon, prostate, breast, gastric and liver cancers, wherein the kit comprises the antibody or fragment according to claim 1.

15. The method of claim 11, wherein the cytotoxic label is a radioisotope label.

16. The method of claim 15, wherein the radioisotope label is selected from 90yttrium ($^{90}Y$) and 111indium ($^{111}In$).

17. The pharmaceutical composition of claim 13, wherein the cytotoxic label is a radioisotope label.

18. The pharmaceutical composition of claim 17, wherein the radioisotope label is selected from 90yttrium ($^{90}Y$) and 111indium ($^{111}In$).

19. An antibody or an antigen binding fragment thereof, wherein the antibody comprises an H chain V region and an L chain V region, wherein the H chain V region and the L chain V region selected from the group consisting of:
   (a) an H chain V region comprising CDRs included in an H chain V region having the amino acid sequence shown in SEQ ID NO: 4, and an L chain V region comprising CDRs included in an L chain V region having the amino acid sequence shown in SEQ ID NO 12; and
   (b) an H chain V region comprising CDRs included in an H chain V region having the amino acid sequence shown in SEQ ID NO: 20, and an L chain V region comprising CDRs included in an L chain V region having the amino acid sequence shown in SEQ ID NO: 28,
and wherein the antibody is capable of binding to a CDH3 polypeptide or a partial peptide thereof.

\* \* \* \* \*